(12) United States Patent
Yamanouchi et al.

(10) Patent No.: US 6,589,723 B2
(45) Date of Patent: Jul. 8, 2003

(54) FLUOROCOMPOUND, SILVER HALIDE PHOTOGRAPHIC LIGHT-SENSITIVE MATERIAL, SURFACTANT, AND WATER-BASED COATING COMPOSITION EMPLOYING SAME

(75) Inventors: Junichi Yamanouchi, Minami-ashigara (JP); Terukazu Yanagi, Minami-ashigara (JP); Tomokazu Yasuda, Minami-ashigara (JP); Nobuo Hamamoto, Minami-ashigara (JP)

(73) Assignee: Fuji Film Co., Ltd., Minami-ashigara (JP)

( * ) Notice: Subject to any disclaimer, the term of this patent is extended or adjusted under 35 U.S.C. 154(b) by 0 days.

(21) Appl. No.: 10/080,702

(22) Filed: Feb. 25, 2002

(65) Prior Publication Data
US 2002/0197571 A1 Dec. 26, 2002

(30) Foreign Application Priority Data
Feb. 26, 2001 (JP) ........................................ 2001-050746

(51) Int. Cl.$^7$ ............................. G03C 1/38; G03C 1/09; G03C 1/85
(52) U.S. Cl. ..................... 430/529; 430/523; 430/539; 430/603; 430/605; 430/634
(58) Field of Search ............................... 430/634, 527, 430/523, 539, 603, 605, 529

(56) References Cited

U.S. PATENT DOCUMENTS 4,347,308 A * 8/1982 Takeuchi et al. ............ 430/634
4,968,599 A * 11/1990 Pitt et al. .................... 430/527
4,999,276 A * 3/1991 Kuwabara et al. ........... 430/527

FOREIGN PATENT DOCUMENTS

| EP | 0 284 331 A1 | 3/1988 |
| JP | 2-141739 A | 5/1990 |
| JP | 3-95550 A | 4/1991 |

* cited by examiner

Primary Examiner—Richard L. Schilling
(74) Attorney, Agent, or Firm—Birch, Stewart, Kolasch & Birch, LLP

(57) ABSTRACT

A fluorocompound denoted by general formula (1) below

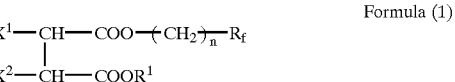

(wherein $R^1$ denotes a substituted or unsubstituted alkyl group having a total of at least six carbon atoms, with $R^1$ not being an alkyl group substituted with a fluorine atom; $R_f$ denotes a perfluoroalkyl group having not more than six carbon atoms; either $X^1$ or $X^2$ denotes a hydrogen atom and the other denotes $SO_3M$; M denotes a cation; and n denotes an integer of not less than 1) was disclosed. A silver halide photographic light-sensitive material having at least one layer comprising a light-sensitive silver halide emulsion layer on a support and comprising a compound denoted by general formula (1) above was also disclosed.

17 Claims, No Drawings

FLUOROCOMPOUND, SILVER HALIDE PHOTOGRAPHIC LIGHT-SENSITIVE MATERIAL, SURFACTANT, AND WATER-BASED COATING COMPOSITION EMPLOYING SAME

TECHNICAL FIELD

The present invention relates to a new fluorocompound and surfactant to which can be imparted surface functions such as water repellency, oil repellency, grime resistance, and electrostatic resistance, and a water-based coating material and silver halide photographic light-sensitive material employing the same.

RELATED ART

Compounds having fluoroalkyl chains are known as surfactants. Various surface property modifications can be conducted based on the unique properties (water repellency, oil repellency, lubricating property, electrostatic resistance, and the like) of fluoroalkyl chains, and they are widely employed in the surface processing of base materials such as fiber, cloth, carpet, and resins. Furthermore, not only can uniform films be formed without repelled spots during film formation when surfactants comprising fluoroalkyl chains (referred to hereinafter as fluorosurfactants) are added to aqueous medium solutions of various matrixes, but an adsorption layer of the surfactant can be formed on the matrix surface, imparting the above-mentioned unique properties of fluoroalkyl chains to the film surface.

Various surfactants are employed in photographic light-sensitive materials, performing important roles. Photographic light-sensitive materials are usually manufactured by applying multiple coating solutions comprising aqueous solutions of a hydrophilic colloidal binder (such as gelatin) on a support member to form multiple layers. Often, multiple hydrophilic colloidal layers are simultaneously applied in multiple layers. These layers include antistatic layers, undercoating layers, antihalation layers, silver halide layers, intermediate layers, filter layers, and protective layers. Various substances are added to individual layers to impart specific functions. Furthermore, polymer latex is sometimes incorporated into hydrophilic colloidal layers to improve the physical properties of the films. To incorporate highly water-insoluble functional groups such as color couplers, ultraviolet absorbing agents, fluorescent whitening agents, and lubricants into hydrophilic colloidal layers, these substances are sometimes dispersed and emulsified as is in hydrophilic colloidal solutions or as solutions of high-boiling-point organic solvents such as phosphoric ester compounds and phthalic ester compounds, and employed in the preparation of coating solutions. Generally, in this manner, photographic light-sensitive materials are comprised of various hydrophilic colloidal layers, and in the course of manufacturing, coating solutions comprising various substances are required to permit uniform high-speed coating without the drawbacks of repelled spots and coating irregularity. To fulfill such demands, surfactants are often added to coating solutions as adjuvants.

Additionally, photographic light-sensitive materials come into contact with a variety of substances during manufacturing, photographing, and developing. For example, during processing, when the light-sensitive material is wound up, the backing layer formed on the back surface of the support sometimes comes into contact with the front surface. Furthermore, in the course of conveying during processing, there is sometimes contact with stainless steel and rubber rollers. Upon contact with such materials, the surface of the light-sensitive material (gelatin layer) tends to develop a positive charge, sometimes causing unwanted discharge leaving behind undesirable exposure traces (known as static marks) on the light-sensitive material. Compounds comprising fluorine atoms are effective at reducing the electrostatic property of the gelatin, and fluorine surfactants are often added.

Thus, surfactants, particularly fluorine surfactants, are employed as materials functioning both as coating adjuvants imparting uniform properties to the coating film and as antistatic agents in the photographic light-sensitive material. Specific examples are disclosed in JP-A-49-46733, JP-A-51-32322, JP-A-57-654228, JP-A-64-536, JP-A-2-141739, JP-A-3-95550, and JP-A-4-248543 (the term "JP-A" as used herein means an "unexamined published Japanese patent application"). However, these materials do not necessarily afford satisfactory performance as regards demands for high sensitivity and high-speed coating in photographic light-sensitive materials of recent years, and further improvement in fluorine surfactants is needed. Generally, short perfluoroalkyl chains are considered advantageous from the viewpoint of decomposition (the decomposition of the compound following use), but the orientation of the fluoroalkyl chain in the coating surface decreases markedly. Accordingly, there is a strong need for the development of a fluorosurfactant with a relatively short fluoroalkyl chain affording both surface orientation (related to the electrostatic property) and coating uniformity.

The present invention has as its object to provide a new fluorocompound and a surfactant comprising the same that permit uniform film formation when employed during film formation while having short perfluoroalkyl groups. A further object of the present invention is to provide an aqueous coating composition capable of forming uniform films having antistatic properties. A still further object of the present invention is to provide a silver halide light-sensitive material imparted with antistatic properties while permitting stable production.

SUMMARY OF THE INVENTION

The foregoing objects are accomplished by the invention to provide a fluorocompound denoted by general formula (1) below.

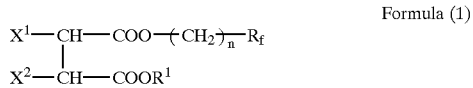

Formula (1)

(wherein $R^1$ denotes a substituted or unsubstituted alkyl group having a total of at least six carbon atoms, with $R^1$ not being an alkyl group substituted with a fluorine atom; $R_f$ denotes a perfluoroalkyl group having not more than six carbon atoms; either $X^1$ or $X^2$ denotes a hydrogen atom and the other denotes $SO_3M$; M denotes a cation; and n denotes an integer of not less than 1).

In the formula (1), $R^1$ preferably denotes a substituted or unsubstituted alkyl group with a total of 6–24 carbon atoms, more preferably, a substituted or unsubstituted alkyl group with a total of 6–18 carbon atoms, and further preferably, an unsubstituted alkyl group with a total of 8–10 carbon atoms.

In the formula (1), n preferably denotes an integer of 1–4, more preferably, 1 or 2.

In the formula (1), it is preferably that when n=1, $R_f$ denotes a heptafluoro-n-propyl group or nonafluoro-n-butyl group, and when n=2, $R_f$ denotes a nonafluoro-n-butyl group.

In the formula (1), M preferably denotes an alkali metal ion, alkali earth metal ion or ammonium ion.

This invention further provides a silver halide photographic light-sensitive material having at least one layer comprising a light-sensitive silver halide emulsion layer on a support and comprising a compound denoted by general formula (1) below in at least one layer thereof Formula (1)

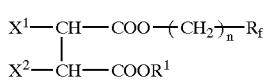

(wherein $R^1$ denotes a substituted or unsubstituted alkyl group having a total of at least six carbon atoms, with $R^1$ not being an alkyl group substituted with a fluorine atom; $R_f$ denotes a perfluoroalkyl group having not more than six carbon atoms; either $X^1$ or $X^2$ denotes a hydrogen atom and the other denotes $SO_3M$; M denotes a cation; and n denotes an integer of not less than 1).

In a preferred embodiment of the present invention, there is a light-insensitive hydrophilic colloidal layer in the outermost layer and said outermost layer comprises the compound denoted by said general formula (1).

In a preferred embodiment of the present invention, at least one of the silver halide emulsions comprised in said silver halide emulsion layers is an emulsion in which not less than 50 percent of the total projection area of the silver halide grains is made up of grains with an aspect ratio of not less than 3, in a more preferred, not less than 8.

In a preferred embodiment of the present invention, at least one of the silver halide comprised in said silver halide emulsion layers is iodobromide, iodochloride, bromochloride or iodochlorobromide.

In a preferred embodiment of the present invention, at least one of the silver halide emulsions comprised in said silver halide emulsion layers is subjected to at least one from among sulfur sensitization, selenium sensitization, gold sensitization, palladium sensitization, or noble metal sensitization This invention further provides a surfactant and a water-based coating composition comprising a fluorocompound denoted by general formula (1) above.

DETAILED DESCRIPTION OF THE INVENTION

The present invention is described in detail below. In the present Specification, the symbol "–" indicates a range having as minimum and maximum the two numbers before and after it, inclusive.

The fluorocompound and surfactant of the present invention will be described first. The fluorocompound of the present invention is denoted by general formula (1) below. The fluorocompound of the present invention may be employed as a surfactant.

In general formula (1), $R^1$ denotes an alkyl group substituted with a total of six or more carbon atoms or unsubstituted. However, $R^1$ does not denote an alkyl group substituted with a fluorine atom. The substituted or unsubstituted group denoted by $R^1$ may have a straight-chain, branching chain, or ring structure. Examples of the above-mentioned substituents are alkylenyl groups, aryl groups, alkoxy groups, halogen atoms other than fluorine, carboxylic ester groups, carbonamide groups, carbamoyl groups, oxycarbonyl groups, and phosphoric ester groups.

The substituted or unsubstituted alkyl group denoted by $R^1$ preferably has a total of 6–24 carbon atoms. Examples of unsubstituted alkyl groups having 6–24 carbon atoms are: n-hexyl groups, n-heptyl groups, n-octyl groups, tert-octyl groups, 2-ethylhexyl groups, n-nonyl groups, 1,1,3-trimethylhexyl groups, n-decyl groups, n-dodecyl groups, cetyl groups, hexadecyl groups, 2-hexyldecyl groups, octadecyl groups, eicosyl groups, 2-octyldodecyl groups, docosyl groups, tetracosyl groups, 2-decyltetradecyl groups, tricosyl groups, cyclohexyl groups, and cycloheptyl groups. Examples of preferred substituted alkyl groups with a total of 6–24 carbon atoms including the carbon atoms in the substituent are: 2-hexenyl groups, oleyl groups, linoleyl groups, linolenyl groups, benzyl groups, β-phenethyl groups, 4-phenylbutyl groups, 6-phenoxyhexyl groups, 12-phenyldodecyl groups, 18-phenyloctadecyl groups, 12-(p-chlorophenyl)dodecyl groups, and 2-(phosphoric diphenyl)ethyl groups.

The substituted or unsubstituted alkyl group denoted by $R^1$ desirably has a total of 6–18 carbon atoms. Preferred examples of unsubstituted alkyl groups having 6–18 carbon atoms are n-hexyl groups, cyclohexyl groups, n-heptyl groups, n-octyl groups, 2-ethylhexyl groups, n-nonyl groups, 1,1,3-trimethylhexyl groups, n-decyl groups, n-dodecyl groups, cetyl groups, hexadecyl groups, 2-hexyldecyl groups, octadecyl groups, and 4-tert-butylcyclohexyl groups. Furthermore, preferred examples of substituted alkyl groups having a total of 6–18 carbon atoms including the carbon atoms in the substituent are: phenethyl groups, 6-phenoxyhexyl groups, 12-phenyldodecyl groups, oleyl groups, linoleyl groups, and linolenyl groups. Of these, $R^1$ is preferably an n-hexyl group, cyclohexyl group, n-heptyl group, n-octyl group, 2-ethylhexyl group, n-nonyl group, cyclohexyl group, n-heptyl group, n-octyl group, 2-ethylhexyl group, n-nonyl group, 1,1,3-trimethylhexyl group, n-decyl group, n-dodecyl group, cetyl group, hexadecyl group, 2-hexyldecyl group, octadecyl group, oleyl group, linoleyl group, or linolenyl group. Straight-chain, cyclic or branching chain unsubstituted alkyl groups having 8–16 carbon atoms are particularly preferred.

In above-recorded general formula (1), $R_f$ denotes a perfluoroalkyl group having not more than six carbon atoms. Here, the term "perfluoroalkyl group" means an alkyl group in which all the hydrogen atoms have been substituted with fluorine atoms. The alkyl group in the perfluoroalkyl group may have a straight-chain, branching chain, or ring structure. Examples of the perfluoroalkyl group denoted by $R_f$ are trifluoromethyl groups, pentafluoroethyl groups, heptafluoro-n-propyl groups, heptafluoroisopropyl groups, nonafluoro-n-butyl groups, undecafluoro-n-pentyl groups, tridecafluoro-n-hexyl groups, and undecafluorocyclohexyl groups. Of these, perfluoroalkyl groups having 2–4 carbon atoms (for example, pentafluoroethyl groups, heptafluoro-n-propyl groups, heptafluoroisopropyl groups, and nonafluoro-n-butyl groups) are preferred, and heptafluoro-n-propyl groups and nonafluoro-n-butyl groups are particularly preferred.

In above-recorded general formula (1), n denotes an integer of not less than 1, preferably 1–4, and more preferably, 1 or 2.

Furthermore, in combinations of n and $R_f$, when n=1, $R_f$ is preferably a heptafluoro-n-propyl group or nonafluoro-n-butyl group, and when n=2, $R_f$ is preferably a nonafluoro-n-butyl group.

In above-recorded general formula (1), either $X^1$ or $X^2$ denotes a hydrogen atom and the other denotes $SO_3M$, where M denotes a cation. Here, preferred examples of the cation denoted by M are alkali metal ions (lithium ion, sodium ion, potassium ion, or the like), alkaline earth metal ions (barium ion, calcium ion, or the like), and ammonium ions. Of these, the most preferred are lithium ions, sodium ions, potassium ions, and ammonium ions.

Specific preferred examples of the fluorocompound denoted by above-recorded general formula (1) are given below; however, the present invention is in no way limited to these specific examples. For simplicity, in the examples of the compounds given below, $X^1$ denotes $SO_3M$ and $X^2$ denotes a hydrogen atom. But $X^1$ can also denote a hydrogen atom and $X^2$ can denote $SO_3M$ in the examples of compounds given below, and those compounds are also specific examples of the fluorocompound of the present invention.

In the structural annotation of the examples of compounds given below, unless specifically stated otherwise, a perfluoroalkyl group means a straight-chain structure. In the abbreviated structural annotation below, groups having the symbols 2EH and 2BO comprise the following groups, respectively:

2EH: 2-ethylhexyl,
2BO: 2-butyloctyl.

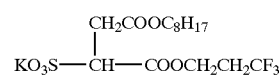

FS-1

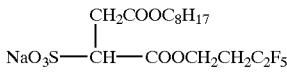

FS-2

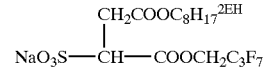

FS-3

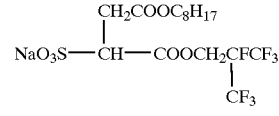

FS-4

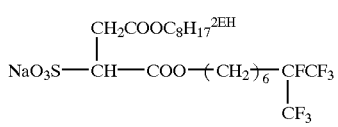

FS-5

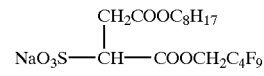

FS-6

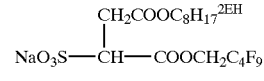

FS-7

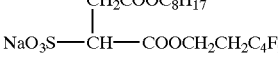

FS-8

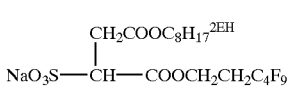

FS-9

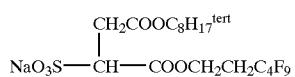

FS-10

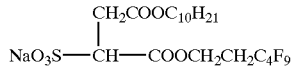

FS-11

-continued

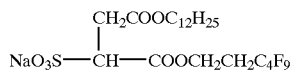

FS-12

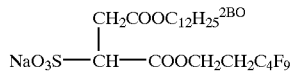

FS-13

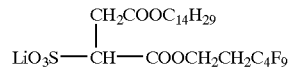

FS-14

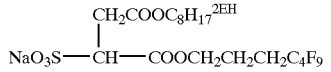

FS-15

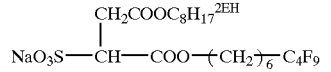

FS-16

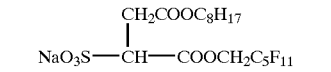

FS-17

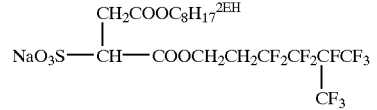

FS-18

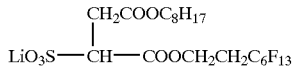

FS-19

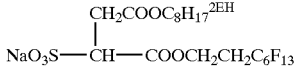

FS-20

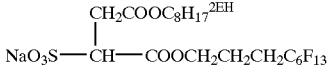

FS-21

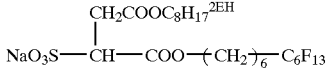

FS-22

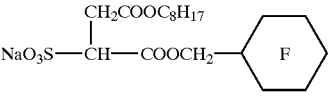

FS-23

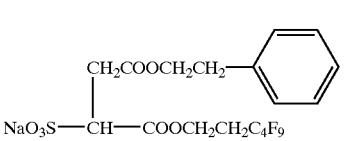

FS-24

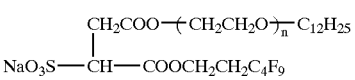

FS-25 n = 1

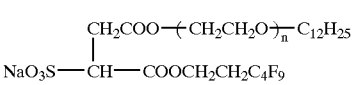

FS-26 n = 2

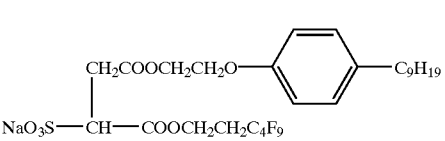

FS-27

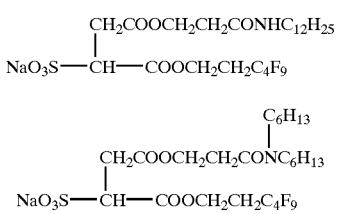

The fluorocompound denoted by above-recorded general formula (1) can be readily synthesized by combination of the usual esterification and sulfonation reactions.

The fluorocompound of the present invention is preferably employed as a surfactant in the various coating compositions for forming layers comprising recording materials (particularly silver halide photographic light-sensitive materials). Use in the formation of the hydrophilic colloid layer of the uppermost layer of the photographic light-sensitive material is particularly desirable in that it yields effective antistatic capability and coating uniformity. Coating compositions incorporating the fluorocompound of the present invention as surfactant are described below.

The water-based coating composition of the present invention comprises the surfactant of the present invention and a solvent in which the surfactant of the present invention is dissolved and/or dispersed. Other components may be appropriately incorporated as needed based on the objective.

An aqueous medium is preferred as the medium in the water-based coating composition of the present invention. Aqueous media include water and mixed solvents of water and organic solvents other than water (for example, methanol, ethanol, isopropyl alcohol, n-butanol, methyl cellosolve, dimethyl formamide, and acetone). In the present invention, the medium of the coating composition desirably comprises not less than 50 mass percent water.

One type of the fluorocompound of the present invention may be employed singly, or two or more types may be mixed and used in the water-based coating composition of the present invention. Other surfactants may also be employed with the fluorocompound of the present invention. Examples of other surfactants suitable for use in combination are various anionic, cationic, and nonionic surfactants. The surfactants employed in combination may be macromolecular surfactants or fluorine surfactants other than the surfactant of the present invention. Anionic or nonionic surfactants are preferred as the surfactants employed in combination. Examples of surfactants suitable for use in combination are those described in JP-A-62-215272 (pp. 649–706), Research Disclosure (RD) Item 17643, pp. 26–27 (December, 1978), RD Item 18716, p. 650 (November 1979), and RD Item. 307105, pp. 875–876 (November, 1989).

Polymer compounds are representative examples of other components that can be incorporated into the water-based coating composition of the present invention. The polymer compounds may be soluble in aqueous media (referred to hereinafter as "soluble polymers") or polymer-in-water dispersions (known as "polymer latexes"). Soluble polymers are not specifically limited; examples are: gelatin, polyvinyl alcohols, casein, agar, gum arabic, hydroxyethyl cellulose, methyl cellulose, and carboxymethyl cellulose. Examples of polymer latexes are homopolymers and copolymers of various vinyl monomers (for example, acrylate derivatives, methacrylate derivatives, acrylamide derivatives, methacrylamide derivatives, styrene derivatives, conjugate diene derivatives, N-vinyl compounds, O-vinyl compounds, vinylnitrile, and other vinyl compounds (such as ethylene and vinylidene chloride)) and dispersions of condensation polymers (such as polyester, polyurethane, polycarbonate, and polyamide). Examples of specific polymer compounds of this type are the polymer compounds described in JP-A-62-215272 (pp. 707–763), RD Item 17643, p. 651 (December, 1978), RD Item 18716, p. 650 (November 1979), and RD Item. 307105, pp. 873–874 (November, 1989).

Other types of compounds may be incorporated into the water-based coating composition of the present invention, or they may be dissolved or dispersed in a medium. For example, when employed in the formation of the structural layers of a photographic light-sensitive material, examples are various couplers, ultraviolet-absorbing agents, anticolor mixing agents, antistatic agents, scavengers, antifogging agents, film-hardening agents, dyes, and antimildew agents. Furthermore, as set forth above, the water-based coating composition of the present invention is desirably employed in the formation of the hydrophilic colloid layer of the uppermost layer of photographic light-sensitive materials. In that case, other surfactants, matting agents, lubricants, colloidal silica, gelatin plasticizers, and the like may be incorporated into the coating composition in addition to a hydrophilic colloid (gelatin, for example) and the fluorine composition of the present invention.

The quantity employed of the fluorocompound of the present invention is not specifically limited. However, the quantity employed may be freely determined based on the structure and use of the compound employed, the type and quantity of the substances incorporated into the water-based composition, the structure of the medium, and the like. For example, when employing the water-based coating composition of the present invention as the coating solution for the hydrophilic colloid (gelatin) layer of the uppermost layer of a silver halide photographic light-sensitive material, the concentration in the coating composition of the fluorocompound of the present invention is desirably 0.003–0.5 mass percent, and preferably 0.03–5 mass percent based on the gelatin solid component.

The silver halide photographic light-sensitive material of the present invention is characterized in that at least one layer comprising a light-sensitive silver halide emulsion layer is present on a support and the fluorocompound of the present invention is incorporated into at least one layer. As an example of a preferred implementation mode of the silver halide photographic light-sensitive material of the present invention, there is a light-insensitive hydrophilic colloid layer as the outermost layer and this outermost layer comprises the fluorocompound of the present invention.

The silver halide photographic light-sensitive material of the present invention can be manufactured by coating one or more of the water-based coating compositions of the present invention on a support. The method of applying the coating composition is not specifically limited, it being possible to employ a slide bead coating method, slide curtain coating method, extrusion curtain coating method, or extrusion bead coating method. Of these, the slide bead coating method is preferred.

Various materials employed in the silver halide photographic light-sensitive material of the present invention will be described below in an example of a silver halide color photographic light-sensitive material.

Silver halide grains suited to use in the silver halide photographic light-sensitive material of the present invention may be in the form of regular cubic, octahedral, or tetrakaidecahedral crystals, irregular spherical or platelike crystals, crystals having twin-plane or other crystalline defects, or combinations of the same. Platelike grains are particularly preferred.

In platelike granular emulsions, more than 50 percent of the total projected area is desirably made up of grains with an aspect ratio of not less than three. The projected area and aspect ratio of the platelike grains referred to here can be measured in electron microscope photographs by the carbon replica method in which shadows are cast together with reference latex spheres. When the platelike grains are viewed in a direction perpendicular to the main plane, they are usually hexagonal, triangular, or round in form. The value obtained by dividing the diameter (circle equivalent diameter) corresponding to a circle of area equal to the projected area by the thickness is the aspect ratio. The higher the ratio of hexagonally shaped platelike grains the better, and the ratio of the length of adjacent hexagonal edges is desirably not greater than 1:2.

As regards the effect of the present invention, since better photographic performance is achieved the higher the aspect ratio, not less than 50 percent of the total projected area of the platelike granular emulsion is desirably comprised of grains with an aspect ratio of not less than 8, preferably not less than 12. Since the greater the aspect ratio, the higher the variation coefficient of grain size distribution tends to become, an aspect ratio of not less than 50 is normally desirable.

The mean grain diameter of the silver halide grains is desirably 0.2–10.0, $\mu$m, more preferably 0.5–5.0 $\mu$m, as a mean circle equivalent diameter. The term "mean circle equivalent diameter" means the diameter of a circle having an area equal to the projected area of the parallel main surface of the grain. The projected area of the grain is measured as the area on an electron microscope photograph corrected for photographic magnification. As a mean sphere equivalent diameter, the diameter is desirably 0.1–5.0 $\mu$m, preferably 0.6–2.0 $\mu$m. These ranges yield photographic emulsions with the best relation of sensitivity/grain shape ratio.

For platelike grains, an average thickness of 0.05–1.0 $\mu$m is desirable. The term average circle equivalent diameter referred to here is the average value of the circle equivalent diameter of not fewer than 1,000 grains collected at random in a uniform emulsion. This is also true for the average thickness.

The silver halide grains may be in the form of a monodispersion or polydispersion.

The platelike grain emulsion desirably comprises the opposing (111) main planes and the lateral planes connected to these main planes. At least one twin plane surface is desirably present between the main planes. Normally, two twin planes are desirably observed in the platelike grain emulsion employed in the present invention. The gap between the two twin planes can be made less than 0.012 $\mu$m as described in U.S. Pat. No. 5,219,720. Furthermore, the value of the distance between main planes (111) divided by the gap between the twin planes can be made 15 or greater as described in JP-A-5-249585. In the present invention, not more than 75 percent of the total lateral planes connecting opposing main planes (111) of the platelike grain emulsion are desirably comprised of planes (111). Here, the statement that not more than 75 percent are comprised of planes (111) means that crystallographic planes other than the (111) planes are present in a ratio of greater than 25 percent of the total lateral planes. It will be understood that these planes are normally the (100) planes, but cases where they are some other plane, such as the (110) plane or a plane with a higher index, are also included. The effect of the present invention decreases markedly when less than 70 percent of the total lateral planes are comprised of plane (111).

Examples of silver halide solvents suitable for use in the present invention are (a) the organic thioethers described in U.S. Pat. Nos. 3,271,157, 3,531,289, and 3,574,628 and JP-A-54-1019, Sho 54-158917; (b) the thiourea derivatives described in JP-A-53-82408, JP-A-55-77737 and JP-A-55-2982; (c) the silver halide solvents having thiocarbonyl groups incorporating oxygen or sulfur atoms and nitrogen atoms described in JP-A-53-144319; (d) the imidazoles described in JP-A-54-100717; (e) ammonia; and (f) thiocyanates.

Solvents of particular preference are thiocyanate, ammonia, and tetramethylthiourea. The quantity of solvent employed varies by type, but in the case of thiocyanate, is preferably $1 \cdot 10^{-4}$ mol to $1 \cdot 10^{-2}$ mol per mol of silver halide.

European Patent No. 515894A1 can be referred to for the method of changing the plane index of the lateral planes of the platelike grain emulsion. The polyalkylene oxide compound described in U.S. Pat. No. 5,252,453 can also be employed. The plane index modifying agents described in U.S. Pat. Nos. 4,680,254, 4,680,255, 4,680,256, and 4,684,607 may also be employed as effective methods. Commonly employed photographic spectral sensitization pigments may also be employed as plane index modifiers similar to those set forth above.

So long as they satisfy the above-stated requirements, the silver halide emulsion can be prepared by a variety of methods. Normally, preparation of the platelike grain emulsion comprises the three basic steps of nucleation, maturation, and growth. In the nucleation step, the use of the gelatin comprising a small quantity of methionine described in U.S. Pat. Nos. 4,713,320 and 4,942,120; the conducting of nucleation with high pBr described in U.S. Pat. No. 4,914,014; and the conducting of nucleation in a short period as described in JP-A-2-222940 are extremely effective in the nucleation step of the platelike grain emulsion employed in the present invention. The conducting of maturation in the presence of a low-concentration base described in U.S. Pat. No. 5,254,453 and the conducting of maturation at high pH described in U.S. Pat. No. 5,013,641 are useful in the step of maturing the platelike grain emulsion. The conducting of growth at low temperature described in U.S. Pat. No. 45,248,587 [sic] and the use of silver iodide micrograins described in U.S. Pat. Nos. 4,672,027 and 4,693,964 are particularly effective in the growth step of the platelike grain emulsion. It is also desirable to conduct growth through maturation by adding silver bromide, silver iodobromide, and silver chloroiodobromide micrograin emulsions. It is also possible to feed the above-listed micrograin emulsions with the stirring device described in JP-A-10-43570.

The silver halide emulsion is desirably silver iodobromide, iodochloride, bromochloride, or iodochlorobromide. It is preferably comprised of silver iodobromide or iodochlorobromide. In the case of iodochlorobromide, silver chloride may also be incorporated, but the silver chloride content is desirably not more than 8 molar percent, preferably not more than 3 molar percent, or even 0 molar percent. Since the variation coefficient of the grain size distribution is desirably not greater than 25 percent, the silver iodide content is desirably not greater than 20 molar percent. Reducing the silver iodide content facilitates a reduction in the variation coefficient of the grain size distribution of the platelike grain emulsion. A variation coefficient in grain size distribution in the platelike grain emulsion of not greater than 20 percent and a silver iodide content of not greater than 10 molar percent are particularly desirable. Irrespective of the silver iodide content, a variation coefficient of the distribution of the silver iodide content between grains of not greater than 20 percent is desirable, and not greater than 10 percent is preferred.

With regard to the silver iodide distribution, the silver halide emulsion preferably has an intragranular structure. In that case, the structure of the silver iodide distribution can be a double structure, triple structure, quadruple structure, or structure of some higher order.

For example, the structure of the silver halide emulsion is desirably a triple structure grain comprising silver bromide, silver iodide, and silver bromide, or a higher order structure. The boundary of the silver iodide content between structures can be sharp or change continuously and gradually. Normally, measurement of the silver iodide content by powder X-ray diffraction does not reveal two sharp peaks of differing silver iodide contents, but an X-ray diffraction profile trailing in the direction of high silver iodide content.

It is further desirable for the silver iodide content in the phase on the inside to be higher than the silver iodide content on the surface. The silver iodide content of the phase on the inside is desirably at least 5 molar percent, preferably at least 7 molar percent, higher than that of the surface.

When the silver halide emulsion comprises platelike grains, the platelike grains have a dislocation line. The dislocation line of platelike grains can be observed, for example, by the direct method employing a transmission electron microscope at low temperature described by J. F. Hamilton, Phot. Sci. Eng., 11, 57, (1967), and T. Shiozawa, J. Soc. Phot. Sci. Japan, 35, 213 (1972). That is, silver halide grains removed from the emulsion while being careful not to apply pressure of a degree that would generate a dislocation line in the grains are placed on a mesh used for electron microscope observation, and while cooling the sample to prevent damage (printout and the like) by the electron beam, the sample is observed by transmission. At that time, the thicker the grains, the less the tendency for the electron beam to pass through. Thus, clear observation is possible by a method employing high-voltage (not less than 200 kV for grains with a thickness of 0.25 $\mu$m) electron microscopy. From photographs of grains obtained by such methods, it is possible to calculate the position and number of dislocation lines for each grain when viewed from a direction perpendicular to the main plane.

The number of dislocation lines is preferably an average of not fewer than ten per grain, more preferably an average of not fewer than 20 per grain. When dislocation lines are densely present, or when mutually intersecting dislocation lines are observed, there are times when it is impossible to clearly count the number of dislocation lines per grain. However, in such cases, it is possible to make a rough count of degree as to whether there are 10 lines, 20 lines, or 30 lines, and make a clear distinction from the case where there are only several lines. The average number of dislocation lines per grain is counted for at least 100 grains and the average is calculated.

The silver halide grains may be subjected to at least one from among sulfur sensitization, selenium sensitization, gold sensitization, palladium sensitization, or noble metal sensitization at any time during the silver halide emulsion manufacturing process. Two or more sensitization methods are desirably employed in combination. Various types of emulsion can be prepared based on whether chemical sensitization is employed and when. There are types where a chemically sensitized nucleus is embedded within the grain, a type where it is buried at a shallow position from the grain surface, and a type where a chemically sensitized nucleus is formed on the surface. Chemically sensitized nuclei can be formed at desired spots based on the conditions used to prepare the emulsion on the basis of the objective. However, it is desirable to form at least one chemically sensitized nucleus near the surface.

One example of a preferred chemical sensitization that can be implemented is chalcogenide sensitization and noble metal sensitization, which can be employed singly or in combination. These chemical sensitizations can be conducted with an active gelatin such as described by T. H. James in *The Theory of the Photographic Process*, 4$^{th}$ ed., Macmillan, 1977, pp. 67–76, and combined with the sulfur, selenium, tellurium, gold, platinum, palladium, indium, or a combination of multiple members of this group of sensitizing agents at pAg 5–10, pH 5–8, and a temperature of 30–80°, described in Research Disclosure, Vol. 120, April, 1974, 12008; Research Disclosure, Vol. 34, June, 1975, 13452; U.S. Pat. Nos. 2,642,361, 3,297,446, 3,772,031, 3,857,711, 3,901,714, 4,266,018, and 3,904,415; British Patent No. 1,315,755. Salts of gold, platinum, palladium, indium, and other noble metals may be employed in noble metal sensitization, of which gold sensitization, palladium sensitization, and the combination of the two are preferred.

In the case of gold sensitization, known compounds such as auric chloride, potassium chloroaurate, potassium aurothiocyanate, gold sulfide, gold selenide, and other known compounds can be employed. In palladium sensitization, secondary and quaternary salts of palladium can be employed. Preferred palladium compounds for use in palladium sensitization are the compounds denoted by $R_2PdX_6$ and $R_2PdX_4$. Here, R denotes a hydrogen atom, alkali metal atom, or ammonium group. X denotes a halogen atom (chlorine, bromine, or iodine atom). Specific examples are $K_2PdCl_4$, $(NH_4)_2PdCl_6$, $Na_2PdCl_4$, $(NH_4)_2PdCl_4$, $Li_2PdCl_4$, $Na_2PDCl_6$, and $K_2PdBr_4$. Gold compounds and palladium compounds are desirably employed in combination with thiocyanates or selenocyanates.

Sulfur sensitization agents suitable for use are hypo- and thiourea compounds, rhodanine compounds, and the sulfur-containing compounds described in U.S. Pat. Nos. 3,857, 711, 4,266,018, and 4,054,457. Chemical sensitization can also be conducted in the presence of a chemical sensitization adjuvant. Useful chemical sensitization adjuvants are compounds known to inhibit fogging in the chemical sensitization process and increase sensitivity, such as azaindene, azapyridazine, and azapyrimidine. Examples of chemical sensitization adjuvant modifying agents are described in U.S. Pat. Nos. 2,131,038, 3,411,914, and 3,554,757; JP-A-58-126526; and above-cited Duffin, *Photographic Emulsion Chemistry*, pp. 138–143.

Gold sensitization is desirably employed in combination in the silver halide emulsion. The preferred quantity of gold sensitizing agent is $1 \cdot 10^{-4}$–$1 \cdot 10^{-7}$ mol, more preferably $1 \cdot 10^{-5}$–$5 \cdot 10^{-7}$ mol, per mol of silver halide. The preferred quantity of palladium compound is $1 \cdot 10^{-3}$–$5 \cdot 10^{-7}$ mol per mol of silver halide. The preferred quantity of thiocyanate compounds and selenocyanate compounds is $5 \cdot 10^{-2}$–$1 \cdot 10^{-6}$ mol per mol of silver halide. The preferred quantity of sulfur sensitizing agent employed for silver halide grains is $1 \cdot 10^{-4}$–$1 \cdot 10^{-7}$ mol, preferably $1 \cdot 10^{-5}$$5 \cdot 10^{-7}$ mol, per mol of silver halide.

Selenium sensitization is a desirable method of sensitizing the silver halide emulsion. Known unstable selenium compounds are employed in selenium sensitization. Specific examples of selenium compounds suitable for use are colloidal metallic selenium, selenoureas (for example, N,N-dimethylselenourea and N,N-diethylselenourea), selenoketones, and selenoamides. Selenium sensitization is desirably employed in combination with either or both of sulfur sensitization and noble metal sensitization. For example, thiocyanates are desirably added prior to the addition of the above-described spectral sensitization pigments and chemical sensitizing agents. More preferably, they are added after grain formation, and still more preferably, after the end of the desalting step. During chemical sensitization, it is also desirable to add thiocyanates. That is, during the chemical sensitization step, it is desirable to add thiocyanates at least twice. Examples of thiocyanates suitable for use are potassium thiocyanate, sodium thiocyanate, and ammonium thiocyanate. Thiocyanates are usually dissolved in an aqueous solution or a water-soluble solvent and added. The quantity added is $1 \cdot 10^{-5} – 10^{-2}$ mol, preferably $5 \cdot 10^{-5} – 5 \cdot 10^{-3}$ mol, per mol of silver halide.

Gelatin is usefully employed as a protective colloid during preparation of silver halide emulsions and as a binder in other hydrophilic colloid layers. However, other hydrophilic colloids may also be employed. For example, it is also possible to employ gelatin derivatives, graft polymers of gelatin and other polymers, albumin, casein, and other proteins; hydroxyethyl cellulose, carboxymethyl cellulose, cellulose sulfuric esters, and other cellulose derivatives, sodium alginate, starch derivatives, and other sugar derivatives; polyvinyl alcohols, polyvinyl alcohol partial acetals, polyvinyl imidazoles, polyvinyl pyrazoles, and various other homopolymeric and copolymeric synthetic hydrophilic macromolecular substances.

In addition to lime-treated gelatins, acid-treated gelatins and enzyme-treated gelatins such as those described in Bull. Soc. Sci. Photo. Japan. No. 16, p. 30 (1966) may also be employed, as well as hydrolysis products of gelatins and enzyme decomposition products of gelatins.

After washing the emulsion obtained to remove salt, it is desirably dispersed again in a protective colloid. The temperature at which water washing is performed may be selected based on the objective, but the selection is desirably made-within a range of 5–50° C. The pH during water washing may be selected based on the objective, but the selection is desirably made within a range of 2–10, and preferably 3–8. The pAg during water washing may be selected based on the objective, but the selection is desirably made within a range of 5–10. The method of water washing may be selected from among the noodle washing method, dialysis using a semipermeable membrane, centrifugation, coagulation and settling, and ion exchange. In coagulation and settling, a selection can be made among methods employing sulfates, methods employing organic solvents, methods employing water-soluble polymers, methods employing gelatin derivatives, and the like.

During emulsion preparation, for example, during grain formation, desalting, chemical sensitization, and prior to coating, the presence of metallic ion salts is desirable based on the objective. Addition during grain formation is desirable in cases where the grains are doped and addition after grain formation and before completion of chemical sensitization is desirable when employed to modify the grain surface or as chemical sensitizing agents. The entire grain may be doped, or only the grain core, grain shell, or epitaxial portion, or base grains may be doped. Examples of metallic ions that are suitable for use are Mg, Ca, Sr, Ba, Al, Sc, Y, LaCr, Mn, Fe, Co, Ni, Cu, Zn, Ga, Ru, Rh, Pd, Re, Os, Ir, Pt, Au, Cd, Hg, Tl, In, Sn, Pb, and Bi. These may be added in the form of ammonium salts, acetates, nitrates, sulfates, phosphates, hydroxides, hexadentate complexes, tetradentate complexes, and other salts that can be dissolved during grain formation. Examples are $CdBr_2$, $CdCl_2$, $Cd(NO_3)_2$, $Pb(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, and $K_4Ru(CN)_6$. The ligands of coordination compounds may be selected from among halo, aquo, cyano, cyanate, thiocyanate, nitrosyl, thionitrosyl, oxo, and carbonyl ligands. These metallic compounds may be employed singly or in combinations of two, three, or more.

The metallic compounds are desirably dissolved in water, methanol, acetone, or some other suitable solvent for addition. The method of adding a hydrogen halide aqueous solution (such as HCl or HBr) or an alkali halide (such as KCl, NaCl, KBr, and NaBr) may be employed to stabilize the solution. As needed, an acid or alkali may also be added. The metallic compound may be added to the reaction vessel prior to or during grain formation. Alternatively, it may be added to a water-soluble silver salt (such as $AgNO_3$) or an alkali halide water-soluble salt (such as NaCl, KBr, KI), and added continuously during silver halide grain formation. Furthermore, a solution separate from the water-soluble silver salt and alkali halide may be prepared and continuously added at the appropriate time during grain formation. The combination of various addition methods is also desirable.

There are also cases in which adding a chalcogenide compound such as described in U.S. Pat. No. 3,772,031 during preparation of the emulsion is effective. In addition to S, Se, and Te, the incorporation of cyanates, thiocyanates, selenocyanates, carbonates, phosphates, and acetates is also acceptable.

The use of an oxidizing agent for silver during the process of manufacturing the emulsion is desirable. However, silver nuclei imparting improved sensitivity achieved through reduction sensitization of the grain surface must remain to a certain degree. In particular, compounds converting to silver ions the extremely minute silver grains produced as by-products in the silver halide grain formation step and chemical sensitization step are effective. The silver ions produced here may form silver salts that are little soluble in water, such as silver halides, silver sulfides, and silver selenide, or may form silver salts that are readily soluble in water, such as silver nitrate.

Preferred oxidizing agents are inorganic oxidizing agents such as thiosulfonates and organic oxidizing agents such as quinones.

To prevent fogging during the process of manufacturing, storing, or photographically processing the light-sensitive material, or to stabilize the photographic properties thereof, various compounds may be incorporated into the photographic emulsion employed in the present invention. Numerous compounds known to be antifogging agents and stabilizers may be added, such as thiazoles in the form of benzothiazolium salt, nitroimidazole salt, nitrobenzimidazole salt, chlorobenzimidazole salt, bromobenzimidazole salt, mercaptothioazoles, mercaptobenzothiazoles, mercaptobenzimidazoles, mercaptothiadiazoles, aminotriazoles, benzotriazoles, nitrobenzotriazoles, mercaptotetrazoles, (particularly 1-phenyl-5-mercaptotetrazoles); mercaptopyrimidines; mercaptotriazines; thioketo compounds such as oxadolinethione; azaindenes such as triazaindenes, tetraazaindenes (particularly 4-hydroxy-substituted (1,3,3a,7)tetraazaindenes), and pentaazaindenes. The compounds described in U.S. Pat. Nos. 3,954,474 and 3,982,947 and in JP-A-52-28660 may be employed. One preferred compound is that described in JP-B-07-78597 (the term "JP-B" as used herein means an "examined published Japanese patent application"). Antifogging agents and stabilizers may be added at various times based on the objective, such as before grain formation, during grain formation, after grain formation, during the water washing step, during dispersion following water washing, before chemical sensitization, during chemical sensitization, after chemical sensitization, and before coating. In addition to adding these compounds during emulsion preparation to achieve the original effects of preventing fogging and stabilizing, they may also be added to control the crystal walls of the grains, reduce the size of the crystals, reduce the solubility of the crystals, control chemical sensitization, and control pigment disposition.

Layer arrangements, silver halide emulsions, dye formation couplers, functional couplers such as DIR couplers, various additives, and development usable in emulsions and photosensitive materials using the emulsions are described in European Patent No. 0565096A1 (laid open in Oct. 13, 1993) and the patents cited in it, the disclosures of which are herein incorporated by reference. The individual items and the corresponding portions are enumerated below.

1. Layer arrangements: p. 61(ll. 23–35, pp. 61(l. 41)-62(l. 14)
2. Interlayers: p. 61(ll. 36–40)
3. Interlayer effect donor layers: p. 62(ll. 15–18)
4. Halogen compositions of silver halide: p. 62(ll. 21–25)
5. Crystal habits of silver halide: p. 62(ll. 26–30)
6. Size of silver halide grains: p. 62(ll. 31–34)
7. Methods of emulsion preparation: p. 62(ll. 35–40)
8. Size distribution of silver halide grains: p. 62(ll. 41–42)
9. Tabular grains: p. 62(ll. 43–46)
10. Internal structures of grains: p. 62(ll. 47–53)
11. Latent image formation types of emulsions: pp. 62(l. 54)-63(l. 5)
12. Physical ripening-chemical ripening of emulsions: p. 63(ll. 6–9)
13. Usage of emulsion mixtures: p. 63(ll. 10–13)
14. Fogged emulsions: p. 63(ll. 14–31)
15. Non-light-sensitive emulsions: p. 63(ll. 32–43)
16. Silver coating amount: p. 63(ll. 49–50)
17. Photographic additives: described in Research Disclosure (RD) Item 17643 (December, 1978), RD Item 18716 (November, 1979), and RD Item 307105 (November, 1989), the disclosures of which are herein incorporated by reference. The individual items and the corresponding portions are presented below.

| Additives | RD17643 | RD18716 | RD307105 |
|---|---|---|---|
| Chemical sensitizers | p. 23 | p. 648 (right column) | p. 866 |
| Sensitivity increasing agents | | p. 648 (right column) | |
| Spectral sensitizer and super sensitizer | pp. 23–24 | p. 648 (right column)–649 (right column) | pp. 866–868 |
| Brighteners | p. 24 | p. 647 (right column) | p. 868 |
| Antifoggants and stabilizers | pp. 24–25 | p. 649 (right column) | pp. 868–870 |
| Light absorbent, filter dye and ultraviolet absorbents | pp. 25–26 | p. 649 (right column)–650 (left column) | p. 873 |
| Stain preventing agents | p. 25, right column | p. 650 (left to right columns) | p. 872 |
| Dye image stabilizer | p. 25 | p. 650 (left column) | p. 872 |

-continued

| Additives | RD17643 | RD18716 | RD307105 |
|---|---|---|---|
| Hardening agents | p. 26 | p. 651 (left column) | pp. 874–875 |
| Binder | p. 26 | p. 651 (left column) | pp. 873–874 |
| Plasticizers and lubricants | p. 27 | p. 650 (right column) | p. 876 |
| Coating aids and surface active agents (which can be used in place of or with the fluoride compounds.) | pp. 26–27 | p. 650 (right column) | pp. 875–876 |
| Antistatic agents | p. 27 | p. 650 (right column) | pp. 876–877 |
| Matting agent | | | pp. 878–879 |

18. Formaldehyde scavengers: p. 64(ll. 54–57)
19. Mercapto-based antifoggants: p. 65(ll. 1–2)
20. Releasing agents, e.g. fogging agent: p. 65(ll. 3–7)
21. Dyes: p. 65(ll. 7–10)
22. General color couplers: p. 65(ll. 11–13)
23. Yellow, magenta, and cyan couplers: p. 65(ll. 14–25)
24. Polymer couplers: p. 65(ll. 26–28)
25. Diffusing dye forming couplers: p. 65(ll. 29–31)
26. Colored couplers: p. 65(ll. 32–38)
27. General functional couplers: p. 65(ll. 39–44)
28. Bleaching accelerator release couplers: p. 65(ll. 45–48)
29. Development accelerator release couplers: p. 65(ll. 49–53)
30. Other DIR couplers: pp. 65(l. 54)-66(l. 4)
31. Coupler diffusing methods: p. 66(ll. 5–28)
32. Antiseptic and antifungal agents: p. 66(ll. 29–33)
33. Types of light-sensitive materials: p. 66(ll. 34–36)
34. Light-sensitive layer film thickness and swell speed: pp. 66(l. 40)-67(l. 1)
35. Back layers: p. 67(ll. 3–8)
36. General development processing: p. 67(ll. 9–11)
37. Developers and developing agents: p. 67(ll. 12–30)
38. Developer additives: p. 67(ll. 31–44)
39. Reversal processing: p. 67(ll. 45–56)
40. Processing solution aperture ratio: pp. 67(l. 57)-68(l. 12)
41. Development time: p. 68(ll. 13–15)
42. Bleach-fix, bleaching, and fixing: pp. 68(l. 16)-69(l. 31)
43. Automatic processor: p. 69(ll. 32–40)
44. Washing, rinsing, and stabilization: pp. 69(l. 41)-70(l. 18)
45. Replenishment and reuse of processing solutions: p. 70(ll. 19–23)
46. Incorporation of developing agent into light-sensitive material: p. 70(ll. 24–33)
47. Development temperature: p. 70(ll. 34–38)
48. Application to film with lens: p. 70(ll. 39–41)

It is also possible to use a bleaching solution, described in European Patent No. 602600, which contains 2-pyridinecarboxylic acid or 2,6-pyridinedicarboxylic acid, ferric salt such as ferric nitrate, and persulfate. When this bleaching solution is to be used, it is preferable to carry out a stop step and a washing step between the color development step and the bleaching step, and use organic acid such as acetic acid, succinic acid, or maleic acid as the stop solution. Furthermore, for the purposes of pH adjustment and bleaching fog, the bleaching solution preferably contains 0.1 to 2 mols/litter (litter will be referred to as "L" hereinafter) of organic acid such as acetic acid, succinic acid, maleic acid, glutaric acid, or adipic acid.

EXAMPLES

The present invention will be specifically explained with reference to the following examples. The materials, regents, ratios, procedures and so forth shown in the following examples can be optionally changed so long as such change does not depart from the spirit of the present invention. Therefore, the scope of the present invention is not limited by the following examples.

Synthesis Example 1

Synthesis of Example Compound FS-8

1-1: Synthesis of monooctyl maleate

A 72 mL (0.53 mol) quantity of triethylamine was slowly added dropwise to 49 g (0.50 mol) of maleic anhydride, 65 g (0.50 mol) of octanol, and 200 mL of chloroform in an ice bath while maintaining a temperature of not greater than 30° C. When the dropwise addition had been completed, stirring was conducted for 1 hr at room temperature. Subsequently, 400 mL of chloroform was added, the organic phase was washed with 1 mol/L of hydrochloric acid, the organic phase was dried with sodium sulfate, and the solvent was distilled off under reduced pressure, yielding 114 g of monoctyl maleate in the form of a colorless transparent oily compound.

1-2: Synthesis of maleic acid monooctylester monochloride (octyl 3-chloroformylacrylate)

To 104 g (0.5 mol) of phosphorus pentachloride was slowly added dropwise 114 g (0.5 mol) of monooctyl maleate while maintaining a temperature of not greater than 30° C. When the dropwise addition had been completed, stirring was conducted for 1 hr at room temperature. Subsequently, the mixture was heated to 60° C., the pressure was reduced with an aspirator, and the phosphorus oxychloride produced was distilled off, yielding 113 g (yield of 92 percent) of maleic acid monooctylester monochloride in the form of an oily yellow compound.

1-3: Synthesis of mono-3,3,4,4,5,5,6,6,6-nonafluorohexyl monooctylmaleate

A 120 g (0.45 mol) quantity of 3,3,4,4,5,5,6,6,6-nonafluorohexanol and 40.4 mL (0.50 mol) of pyridine were dissolved in 200 mL of chloroform and cooled in an ice bath. While maintaining an internal temperature of not greater than 20° C., 113 g (0.45 mol) of maleic acid monooctylester monochloride was added dropwise. When the dropwise addition had been completed, the mixture was stirred for 1 hr at room temperature. Subsequently, 1,000 mL of ethyl acetate was added, the organic phase was washed with water, saturated sodium bicarbonate aqueous solution, and saturated sodium chloride aqueous solution. The organic phase was recovered, the organic solvent was removed by distillation under reduced pressure, and the product was refined by silica gel chromatography (hexane/chloroform: 10/0-6/4 v/v), yielding 139 g (yield of 65 percent) of the targeted compound in the form of a colorless transparent oily compound.

1-4: Synthesis of sodium mono-3,3,4,4,5,5,6,6,6-nonafluorohexylmonooctyl sulfosuccinate (FS-8)

A 139 g (0.29 mol) quantity of mono-3,3,4,4,5,5,6,6,6-nonafluorohexyl monooctylmaleate, 33.5 g (0.32 mol) of sodium hydrogensulfite, and 140 mL of water-ethanol (1/1 ratio by volume) were added and refluxed with heating for 10 hr. Subsequently, 1,000 mL of chloroform was added, the organic phase was washed with a saturated sodium chloride aqueous solution, the organic phase was recovered, the organic solvent was distilled off under reduced pressure, the product was recrystallized from 500 mL of toluene, and crystals were precipitated by cooling in an ice bath. Finally, the crystals were filtered out, yielding 49 g (yield of 29 percent) of the targeted compound (FS-8) in the form of colorless, transparent crystals.

The melting point and $^1$H-NMR data of the compound obtained were as follows:

mp: 250–254;

$^1$H-NMR(DMSO-$d_6$):d0.84–0.88(m,3H), 1.25(br,10H), 1.51(br,2H), 2.56–2.65(m,2H), 2.79–2.97(m,2H), 3.62–3.69 (m,1H), 3.97(br,2H), 4.30(m,2H).

Synthesis Example 2

Synthesis of Example Compound FS-9

2-1: Synthesis of maleic acid mono(2-ethylhexyl)ester monochloride

A 4.1 g (20 mmol) quantity of mono(2-ethylhexyl) maleate manufactured by Aldrich Co. was slowly added dropwise to 4.1 g (20 mmol) of phosphorus pentachloride while maintaining a temperature not greater than 30° C. When the dropwise addition had been completed, stirring was conducted for 1 hr at room temperature. Subsequently, the mixture was heated to 60° C., the pressure was reduced with an aspirator, and the phosphorus oxychloride was distilled off, yielding 4.5 g (yield of 92 percent) of maleic acid mono(2-ethylhexyl)ester monochloride in the form of a tea-colored oily product.

2-2: Synthesis of mono-2-ethylhexylmono-3,3-4,4,5,5,6,6,6-nonafluorohexyl maleate A 5.3 g quantity (20 mmol) of 3,3,4,4,5,5,6,6,6-nonafluorohexanol and 2.8 mL (20 mmol) of triethylamine were dissolved in 10 mL of chloroform and cooled in an ice bath. A 4.5 g (18 mmol) quantity of maleic acid mono(2-ethylhexyl)ester was added while maintaining an internal temperature of not greater than 20° C. When the dropwise addition had been completed, the mixture was stirred for 1 hr at room temperature. Subsequently, 50 mL of ethyl acetate was added, and the organic phase was washed with water, a saturated sodium bicarbonate aqueous solution, and a saturated sodium chloride aqueous solution. The organic phase was recovered, the organic solvent was distilled off under reduced pressure, and the product was refined by silica gel chromatography (hexane/chloroform: 10/0-5/5), yielding 4.0 g (yield of 46 percent) of colorless, transparent target compound.

2-3: Synthesis of sodium mono-2-ethylhexyl-mon-3,3,4,4,5,5,6,6,6-nonafluorohexyl sulfosuccinate (FS-9)

A 42.5 g (89.6 mmol) quantity of mono-2-ethylhexylmono-3,3,4,4,5,5,6,6,6-nonafluorohexyl maleate, 10.2 g (98.0 mmol) of sodium hydrogensulfite, and 50 mL of water-ethanol (1/1 ratio by volume) were added and the mixture was refluxed with heating for 2 hr. Subsequently, 1,000 mL of ethyl acetate was added, the organic phase was washed with a saturated sodium chloride aqueous solution, the organic phase was recovered, the organic solvent was distilled off under reduced pressure, the product was recrystallized from 250 mL of toluene, and crystals were precipitated by cooling in an ice bath. Finally, the crystals were filtered out, yielding 21.7 g (yield of 48 percent) of colorless, transparent target compound (FS-9).

The melting point and $^1$H-NMR data of the compound obtained were as follows:

mp: 240–244;

$^1$H-NMR(DMSO-d$_6$):d0.82–0.93(m,6H), 1.13–1.32(m, 8H), 1.50(br,1H), 2.57–2.65(m,2H), 2.84–2.98(m,2H), 3.63–3.68(m,1H), 3.90(d,2H), 4.30(m,2H).

Synthesis Example 3

Synthesis of Example Compound FS-12

3-1: Synthesis of monodecyl maleate

A 73.8 mL (0.53 mol) quantity of triethylamine was slowly added dropwise to 49.0 g (0.50 mol) of maleic anhydride, 93.2 g (0.50 mol) of dodecanol, and 210 mL of chloroform while maintaining a temperature not greater than 30° C. in an ice bath. When the dropwise addition had been completed, the mixture was stirred for 1 hr at room temperature. Subsequently, 1,000 mL of chloroform was added, the organic phase was washed with 1 mol/L of hydrochloric acid, the organic phase was dried with sodium sulfate, the solvent was distilled off under reduced pressure, and a monododecyl maleate was quantitatively obtained in the form of a colorless, transparent solid.

3-2: Synthesis of maleic acid monododecylester monochloride

A 40 mL quantity of chloroform dissolved in 158.8 g (0.558 mol) of monododecyl maleate was slowly added dropwise to 116 g (0.558 mol) of phosphorus pentachloride and 40 mL of chloroform while maintaining a temperature of not greater than 30° C. When the dropwise addition had been completed, the mixture was stirred for 1 hr at room temperature. Subsequently, the mixture was heated to 60° C., the pressure was reduced with an aspirator, and the phosphorus oxychloride produced and chloroform were distilled off, yielding 155.8 g (yield of 92 percent) of maleic acid monododecylester monochloride in the form a tea-colored oily compound.

3-3: Synthesis of monododecylmono-3,3,4,4,5,5,6,6,6-nonafluorohexyl maleate

A 164.64 g (0.623 mol) quantity of 3,3,4,4,5,5,6,6,6-nonafluorohexanol and 49.27 g (0.623 mol) of pyridine were dissolved in 280 mL of chloroform and 155.78 g (0.566 mol) of maleic acid monododecylester monochloride was added dropwise while maintaining an internal temperature of not greater than 20° C. When the dropwise addition had been completed, the mixture was stirred for 1 hr at room temperature. Subsequently, 1,000 mL of chloroform was added, the organic phase was washed with 1 mol/L of hydrochloric acid aqueous solution, the organic phase was recovered, the organic solvent was distilled off under reduced pressure, and the product was refined by silica gel chromatography (hexane/chloroform: 10/0-5/5 (ratio by volume)), yielding 48.2 g (yield of 18 percent) of colorless, transparent, oily target compound.

3-4: Synthesis of sodium monododecylmono-3,3,4,4,5,5,6,6,6-nonafluorohexyl sulfosuccinate (FS-12)

A 48.0 g (90.0 mmol) quantity of monododecylmono-3,3,4,4,5,5,6,6,6-nonafluorohexyl maleate, 10.4 g (99.0 mmol) of sodium hydrogensulfite, and 50 mL of water-ethanol (1/1 ratio by volume) were added and refluxed with heating for 5 hr. Subsequently, 1,000 mL of ethyl acetate was added, the organic phase was washed with a saturated sodium hydrochloride aqueous solution, the organic phase was recovered, and the organic solvent was distilled off under reduced pressure, yielding 12.5 g (yield of 22 percent) of the colorless, transparent compound (FS-12).

The melting point and $^1$H-NMR data of the compound obtained were as follows:

mp: 258–260;

$^1$H-NMR(DMSO-d$_6$):d0.85(t,3H), 1.23(br,18H), 1.51(br, 2H), 2.49–2.51(m,2H), 2.80–2.96(m,2H), 3.60–3.68(m,1H), 3.95(br,2H), 4.28(t,2H).

Synthesis Example 4

Synthesis of Example Compound FS-20

4-1: Synthesis of mono-2-ethylhexylmono-3,3,4,4,5,5,6,6,7,7,8,8,8-tridecafluorooctyl maleate A 142 g (0.39 mol) quantity of 3,3,4,4,5,5,6,6,7,7,8,8,8-tridecafluorooctanol and 59.7 mL (0.43 mL) of triethyl amine were dissolved in 200 mL of chloroform, the mixture was cooled in an ice bath, and 106 g (0.43 mol) of maleic acid mono(2-ethylhexyl)ester monochloride was added dropwise while maintaining an internal temperature of not greater than 20° C. When the dropwise addition had been completed, the mixture was stirred for 2 hr at room temperature. Subsequently, 1,000 mL of chloroform was added, the organic phase was washed with 1 mol/L of hydrochloric acid water and saturated sodium chloride aqueous solution, the organic phase was recovered, the organic solvent was distilled off under reduced pressure, and the mixture was refined by silica gel chromatography (hexane/chloroform: 10/0-6/4 (ratio by volume)), yielding 90 g (yield of 37 percent) of the target compound in the form of a colorless, transparent, oily compound.

4-2: Synthesis of sodium mono-2-ethylhexylmono-3,3,4,4,5,5,6,6,7,7,8,8,8-tridecafluorooctyl sulfosuccinate (FS-20)

A 90.9 g (0.157 mol) quantity of mono-2-ethylhexylmono-3,3,4,4,5,5,6,6,7,7,8,8,8-tridecanfluorooctyl maleate, 17.9 g (0.172 mol) of sodium hydrogensulfite, and 90 mL of water-ethanol (1/1 (ratio by volume)) were added and refluxed with heating for 10 hr. Subsequently, 1,000 mL of chloroform was added, the organic phase was washed with a saturated sodium chloride aqueous solution, the organic phase was recovered, the organic solvent was distilled off under reduced pressure, the product was recrystallized from 300 mL of toluene, and the crystals obtained were filtered out, yielding 50.0 g (yield of 47 percent) of the target compound (FS-20) in the form of colorless, transparent crystals.

The melting point and $^1$H-NMR data of the compound obtained were as follows:

mp: 244–246;

$^1$H-NMR(DMSO-d$_6$):d0.85(t,3H), 1.23(br,18H), 1.51(br, 2H), 2.49–2.51(m,2H), 2.80–2.96(m,2H), 3.60–3.68(m,1H), 3.95(br,2H), 4.28(t,2H).

Example 1

Measurement of the Surface Tension Decreasing Capability of Fluorocompounds

The fluorocompounds of the present invention and fluorosurfactants for comparison (Comparative Compounds FC-1 through 5) shown in Table 1 below were used to prepare 0.1 mass percent aqueous solutions. The dynamic surface tension at 100 msec was measured by the maximum bubble pressure method with the automatic surface tension meter BP-DP3 manufactured by Kyowa Kaimen Kagaku K.K. The dynamic surface tensions measured are given in Table 1 below.

TABLE 1

| Surfactant | Dynamic Surface Tension (mN/s) | Remarks |
|---|---|---|
| FS-3 | 50 | This invention |
| FS-8 | 33 | This invention |
| FS-9 | 34 | This invention |
| FS-11 | 45 | This invention |
| FS-12 | 50 | This invention |
| Comratative Copmound FC-1 | 54 | Comparative Example |
| Comratatve Copmound FC-2 | 65 | Comparative Example |
| Comratative Copmound FC-3 | 58 | Comparative Example |
| Comratative Copmound FC-4 | 50 | Comparative Example |
| Comratative Copmound FC-5 | 60 | Comparative Example |

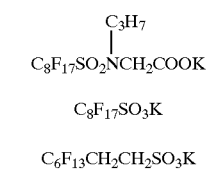

Comparative Compound FC-1

Comparative Compound FC-2

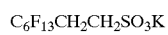

Comparative Compound FC-3

Comparative Compound FC-4

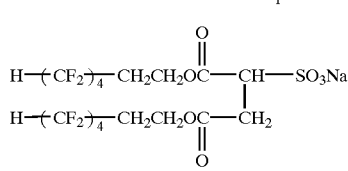

Comparative Compound FC-5

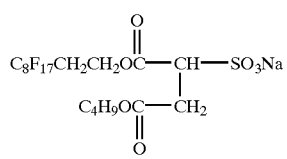

From the results of Table 1, it was clear that the fluorocompound of the present invention had good dynamic surface tension reducing capability.

Example 2

Manufacturing and Evaluation of A Silver Halide Color Photographic Light Sensitive Material (1) Support A support was manufactured as follows.

1) First layer and undercoating layer

Both surfaces of a polyethylene terephthalate support 90 μm in thickness were glow discharge treated with a treatment atmosphere pressure of $2.66 \cdot 10$ Pa, an $H_2O$ partial pressure of 75 percent in the atmospheric gas, a discharge frequency of 30 kHz, an output of 2,500 W, and a processing intensity of 0.5 kV·A·min/m². A coating solution of the composition recorded below was applied by the bar coating method described in JP-B-58-4589 in a coating quantity of 5 mL/m² as the first layer on the support.

| | |
|---|---|
| Electrically conductive micrograin dispersion ($SnO_2/Sb_2O_5$ grain concentration 10 percent aqueous dispersion, mean grain diameter 0.05 μm of secondary aggregates of primary grain diameter 0.005 μm): | 50 mass parts |
| Gelatin | 0.5 mass parts |
| Water | 49 mass parts |
| Polyglycerol polyglycidyl ether | 0.16 mass parts |
| Poly (degree of polymerization 20) oxyethylene sorbitan monolaurate | 0.1 mass parts |

After applying the first layer, the product was wound on a stainless steel core 20 cm in diameter, heat treated for 48 hr at 110° C. (Tg of PEN support: 119° C.), and imparted with a heat history in an annealing treatment. The support was then gripped, and the coating solution of the composition given below was applied in a quantity of 10 mL/m² by the bar application method as the undercoating layer for emulsion on the opposite side from the first layer:

| | |
|---|---|
| Gelatin | 1.01 mass parts |
| Salicylic acid | 0.30 mass parts |
| Resorcinol | 0.40 mass parts |
| Poly (polymerization degree of 10) Oxyethylenenonylphenylether | 0.11 mass parts |
| Water | 3.53 mass parts |
| Methanol | 84.57 mass parts |
| n-Propanol | 10.08 mass parts |

The second and third layers described below were then sequentially coated on the first layer.

2) Second layer (transparent magnetic recording layer)

(i) Dispersion of magnetic powder

Co-coated γ-$Fe_2O_3$ magnetic powder (mean major axis length: 0.25 μm, $S_{BET}$: 39 m²/g, Hc: $6.56 \cdot 10^4$ A/m, ss: 77.1 Am²/kg, sr: 37.4 Am²/kg) in a quantity of 1,100 mass parts, 220 mass parts of water, and 165 mass parts of silane coupling agent [3-(poly(polymerization degree 10)oxyethynyl)oxypropyltrimethoxysilane] were added and kneaded in an open kneader for 3 hr. This crudely dispersed viscous solution was dried overnight at 70° C., the water was removed, and the product was heat treated for 1 hr at 110° C. to obtain surface-treated magnetic grains.

The following formula was then kneaded again for 4 hr in the open kneader:

| | |
|---|---|
| The surface treated magnetic grains | 855 g |
| Diacetyl cellulose | 25.3 g |
| Methyl ethyl ketone | 136.3 g |
| Cyclohexanone | 136.3 g |

Furthermore, the product of the formula given below was finely dispersed for 4 hr at 2,000 rpm in a sandmill (1/4 G sandmill); the media employed was glass beads 1 mm in diameter:

| | |
|---|---|
| The above-described kneaded solution | 45 g |
| Diacetyl cellulose | 23.7 g |
| Methyl ethyl ketone | 127.7 g |
| Cyclohexanone | 127.7 g |

An intermediate solution comprising magnetic material and having the following formula was prepared:

| (ii) Preparation of intermediate solution comprising magnetic material | |
|---|---|
| Above-described magnetic material fine dispersion | 674 g |
| Diacetyl cellulose solution | 24280 g |
| (solid component 4.34 percent, solvent: methyl ethyl ketone/cyclohexanone = 1/1) | |
| Cyclohexanone | 46 g |

These were mixed and stirred in a disperser to prepare the "intermediate solution comprising magnetic material."

(a) Preparation of Grain Dispersion of Sumicorundum AA-1.5 (Mean Primary Grain Diameter 1.5 μm, Specific Surface Area 1.3 m²/g)

| | |
|---|---|
| Sumicorundum AA-1.5 | 152 g |
| Silane coupling agent KBM903 (Shinetsu Silicone Co.) | 0.48 g |
| Diacetyl cellulose solution | 227.52 g |
| (Solid component 4.5 percent, solvent: methyl ethyl ketone/cyclohexanone = 1/1) | |

The above formula was finely dispersed for 4 hr at 800 rpm in a ceramic-coated sandmill (1/4 G sandmill). The medium employed was zirconia beads 1 mm in diameter.

(b) Colloidal Silica Grain Dispersion (Micrograins)

"MEK-ST" manufactured by Nissan Kagaku (K.K.) was employed.

This is a colloidal silica dispersion with a mean primary grain diameter of 0.015 μm and a solid component of 30 percent in a dispersion medium in the form of methyl ethyl ketone.

| (iii) Preparation of second layer coating solution | |
|---|---|
| Above-described intermediate solution comprising magnetic material | 19053 g |
| Diacetyl cellulose solution | 264 g |
| (solid component 4.5 percent, solvent: methyl ethyl ketone/cyclohexanone = 1/1) | |
| Colloidal silica dispersion "MEK-ST" (dispersion (b)), (solid component 30 percent) | 128 g |
| AA-1.5 dispersion (dispersion (a)) | 12 g |
| Millionate MR-400 (made by Japan Polyurethane (K.K.)) dilute solution (solid component 20 percent, dilution solvent: methyl ethyl ketone/cyclohexanone = 1/1) | 203 g |
| Methyl ethyl ketone | 170 g |
| Cyclohexanone | 170 g |

A coating solution obtained by admixing the above was coated in a quantity of 29.3 mL/m² with a wire bar and dried at 110° C. The dry thickness of the magnetic layer was 1.0 μm.

3) Third layer (layer comprising higher fatty ester lubricant)

(i) Preparation of original dispersion solution of lubricant

The "A" solution below was melted by heating to 100° C., added to the "B" solution, and dispersed in a high-pressure homogenizer to prepare an original dispersion solution of lubricant.

| | |
|---|---|
| "A" solution | |
| $C_6H_{13}CH(OH)(CH_2)_{10}COOC_{50}H_{101}$ | 399 mass parts |
| $n\text{-}C_{50}H_{101}O(CH_2CH_2O)_{16}H$ | 171 mass parts |
| Cyclohexanone | 830 mass parts |
| "B" solution | |
| Cyclohexanone | 8600 mass parts |

(ii) Preparation of spherical inorganic grain dispersion

Sperical inorganic grain dispersion (c1) was prepared with the following formula:

| | |
|---|---|
| Isopropyl alcohol | 93.54 mass parts |
| Silane coupling agent KBM 903 (made by Shinetsu Silicone Co.) $(CH_3O)_3Si\text{—}(CH_2)_3\text{—}NH_2$ | 5.53 mass parts |
| Compound-1 | 2.93 mass parts |

$$nC_4H_9\text{—}\underset{\underset{nC_4H_9\text{—}\underset{\underset{C_2H_5}{|}}{CH}\text{—}CH_2OC\text{—}CH_2}{|}}{\overset{\overset{C_2H_5}{|}}{CH}}\text{—}CH_2O\overset{O}{\overset{\|}{C}}\text{—}\underset{\underset{}{}}{CH}\text{—}SO_3Na$$

| | |
|---|---|
| Seahostar KEP 50 | 88.00 mass parts |
| (amorphous spherical silica, mean grain diameter 0.5 μm, made by Nihon Shokubai (K.K.)) | |
| The above-stated formula was stirred for 10 min, after which the following was added: | |
| Diacetone | 88.00 mass parts |

The above-described solution was dispersed for 3 min with an ultrasonic homogenizer, the "Sonifier 450 (made by Branson (K.K.) Co.), with ice cooling and stirring to prepare spherical inorganic grain dispersion c1.

(iii) Preparation of spherical organic polymer grain dispersion

Spherical organic polymer grain dispersion (c2) was prepared with the following formula:

| | |
|---|---|
| XC99-A8808 | 60 mass parts |
| (made by Toshiba Silicone (K.K.), spherical crosslinked polysiloxane grams, mean grain diameter 0.9 μm) | |
| Methyl ethyl ketone | 120 mass parts |
| Cyclohexanone | 120 mass parts |

The mixture was dispersed for 2 hr with an ultrasonic homogenizer, the "Sonifier 450, made by Branson (K.K.)" to prepare spherical organic polymer grain dispersion c2.

(iv) Preparation of third layer coating solution

The following were added to 542 g of the above-described lubricant dispersion original solution to prepare the third layer coating solution.

| | |
|---|---|
| Diacetone alcohol | 5950 g |
| Cyclohexanone | 176 g |
| Ethyl acetate | 1700 g |

| -continued | | |
|---|---|---|
| Above-described Seahostar KEP 50 dispersion (c1) | | 53.1 g |
| Above-described spherical organic polymer grain dispersion (c2) | | 300 g |
| Megafac F-178K (made by Dainippon Ink (K.K.), solid component 30 percent) | | 4.8 g |
| BYK 310 (made by BYK Chemi Japan (K.K.), solid component content 25 percent) | | 5.3 g |

The above-described third layer coating solution was applied over the second layer in a quantity of 10.35 mL/m$^2$, dried at 110° C., and then dried for 3 min at 97° C.

(2) Coating of Light-Sensitive Layers

Next, each of the layers of the following compositions were laminated onto the undercoating surface side of the support to prepare a color negative film. (Composition of light-sensitive layer)

The main materials used in the individual layers are classified as follows. However, the uses of these materials are not restricted to those classified ones.

| ExC: Cyan coupler | UV: Ultraviolet absorbent |
|---|---|
| ExM: Magenta coupler | HBS: High-boiling organic solvent |
| ExY: Yellow coupler | H: Gelatin hardener |
| ExS: Sensitizing dye | |

(The specific compounds are recorded below. Numbers are positioned after the symbols, after which chemical formulas are provided.)

The number corresponding to each component indicates the coating amount in units of g/m$^2$. The coating amount of a silver halide is indicated by the amount of silver.

| 1st layer (1st antihalation layer) | | |
|---|---|---|
| Black colloidal silver | silver | 0.122 |
| Silver bromoiodide emulsion(0.07 μm) | silver | 0.01 |
| Gelatin | | 0.919 |
| ExM-1 | | 0.066 |
| ExC-1 | | 0.002 |
| ExC-3 | | 0.002 |
| Cpd-2 | | 0.001 |
| F-8 | | 0.010 |
| HBS-1 | | 0.005 |
| HBS-2 | | 0.002 |
| 2nd layer (2nd antihalation layer) | | |
| Black colloidal silver | silver | 0.055 |
| Gelatin | | 0.425 |
| ExF-1 | | 0.002 |
| F-8 | | 0.012 |
| Solid disperse dye ExF-7 | | 0.120 |
| HBS-1 | | 0.074 |
| 3rd layer (Interlayer) | | |
| ExC-2 | | 0.050 |
| Cpd-1 | | 0.090 |
| Polyethylacrylate latex | | 0.200 |
| HBS-1 | | 0.100 |
| Gelatin | | 0.700 |
| 4th layer (Low-speed red-sensitive emulsion layer) | | |
| Em-D | silver | 0.577 |
| Em-C | silver | 0.347 |
| ExC-1 | | 0.188 |
| ExC-2 | | 0.011 |
| ExC-3 | | 0.075 |
| ExC-4 | | 0.121 |
| ExC-5 | | 0.010 |
| ExC-6 | | 0.007 |
| ExC-8 | | 0.010 |
| ExC-9 | | 0.020 |
| Cpd-2 | | 0.025 |
| Cpd-4 | | 0.025 |
| HBS-1 | | 0.114 |
| HBS-5 | | 0.038 |
| Gelatin | | 1.474 |
| 5th layer (Medium-speed red-sensitive emulsion layer) | | |
| Em-B | silver | 0.431 |
| Em-C | silver | 0.432 |
| ExC-1 | | 0.154 |
| ExC-2 | | 0.068 |
| ExC-3 | | 0.018 |
| ExC-4 | | 0.103 |
| ExC-5 | | 0.023 |
| ExC-6 | | 0.010 |
| ExC-8 | | 0.016 |
| ExC-9 | | 0.005 |
| Cpd-2 | | 0.036 |
| Cpd-4 | | 0.028 |
| HBS-1 | | 0.129 |
| Gelatin | | 1.086 |
| 6th layer (High-speed red-sensitive emulsion layer) | | |
| Em-A | silver | 1.108 |
| ExC-1 | | 0.180 |
| ExC-3 | | 0.035 |
| ExC-6 | | 0.029 |
| ExC-8 | | 0.110 |
| ExC-9 | | 0.020 |
| Cpd-2 | | 0.064 |
| Cpd-4 | | 0.077 |
| HBS-1 | | 0.329 |
| HBS-2 | | 0.120 |
| Gelatin | | 1.245 |
| 7th Layer (Interlayer) | | |
| Cpd-1 | | 0.094 |
| Cpd-6 | | 0.369 |
| Solid disperse dye ExF-4 | | 0.030 |
| HBS-1 | | 0.049 |
| Polyethylacrylate latex | | 0.088 |
| Gelatin | | 0.886 |
| 8th layer (layer for donating interlayer effect to red-sensitive layer) | | |
| Em-J | silver | 0.293 |
| Em-K | silver | 0.293 |
| Cpd-4 | | 0.030 |
| ExM-2 | | 0.120 |
| ExM-3 | | 0.016 |
| ExM-4 | | 0.026 |
| ExY-1 | | 0.016 |
| ExY-4 | | 0.036 |
| ExC-7 | | 0.026 |
| HBS-1 | | 0.090 |
| HBS-3 | | 0.003 |
| HBS-5 | | 0.030 |
| Gelatin | | 0.610 |
| 9th layer (Low-speed green-sensitive emulsion layer) | | |
| Em-H | silver | 0.329 |
| Em-G | silver | 0.333 |
| Em-I | silver | 0.088 |
| ExM-2 | | 0.36 |
| ExM-3 | | 0.047 |
| ExY-1 | | 0.017 |
| ExC-7 | | 0.007 |
| HBS-1 | | 0.098 |
| HBS-3 | | 0.010 |
| HBS-4 | | 0.077 |
| HBS-5 | | 0.548 |
| Cpd-5 | | 0.010 |
| Gelatin | | 1.470 |

-continued

10th layer (Medium-speed green-sensitive emulsion layer)

| | | |
|---|---|---|
| Em-F | silver | 0.457 |
| ExM-2 | | 0.032 |
| ExM-3 | | 0.029 |
| ExM-4 | | 0.029 |
| ExY-3 | | 0.007 |
| ExC-6 | | 0.010 |
| ExC-7 | | 0.012 |
| ExC-8 | | 0.010 |
| HBS-1 | | 0.065 |
| HBS-3 | | 0.002 |
| HBS-5 | | 0.020 |
| Gelatin | | 0.446 |

11th layer (High-speed green-sensitive emulsion layer)

| | | |
|---|---|---|
| Em-E | silver | 0.794 |
| ExC-6 | | 0.002 |
| ExC-8 | | 0.010 |
| ExM-1 | | 0.013 |
| ExM-2 | | 0.011 |
| ExM-3 | | 0.030 |
| ExM-4 | | 0.017 |
| ExY-3 | | 0.003 |
| Cpd-3 | | 0.004 |
| Cpd-4 | | 0.007 |
| Cpd-5 | | 0.010 |
| HBS-1 | | 0.148 |
| HBS-5 | | 0.037 |
| Polyethylacrylate latex | | 0.099 |
| Gelatin | | 0.939 |

12th layer (Yellow filter Layer)

| | |
|---|---|
| Cpd-1 | 0.094 |
| Solid disperse dye ExF-2 | 0.150 |
| Solid disperse dye ExF-5 | 0.010 |
| Oil-soluble dye ExF-6 | 0.010 |
| HBS-1 | 0.049 |
| Gelatin | 0.630 |

13th layer (Low-speed blue-sensitive emulsion layer)

| | | |
|---|---|---|
| Em-O | silver | 0.112 |
| Em-M | silver | 0.320 |
| Em-N | silver | 0.240 |
| ExC-1 | | 0.027 |
| ExC-7 | | 0.013 |
| ExY-1 | | 0.002 |
| ExY-2 | | 0.890 |
| ExY-4 | | 0.058 |
| Cpd-2 | | 0.100 |
| Cpd-3 | | 0.004 |
| HBS-1 | | 0.222 |
| HBS-5 | | 0.074 |
| Gelatin | | 2.058 |

14th layer (High-speed blue-sensitive emulsion layer)

| | | |
|---|---|---|
| Em-L | silver | 0.714 |
| ExY-2 | | 0.211 |
| ExY-4 | | 0.068 |
| Cpd-2 | | 0.075 |
| Cpd-3 | | 0.001 |
| HBS-1 | | 0.071 |
| Gelatin | | 0.678 |

15th layer (1st protective layer)

| | | |
|---|---|---|
| Silver bromoiodide emulsion(0.07 $\mu$m) | silver | 0.30 |
| UV-1 | | 0.211 |
| UV-2 | | 0.132 |
| UV-3 | | 0.198 |
| UV-4 | | 0.026 |
| F-18 | | 0.009 |
| S-1 | | 0.086 |
| HBS-1 | | 0.175 |
| HBS-4 | | 0.050 |
| Gelatin | | 1.984 |

-continued

16th layer (2nd protective layer)

| | |
|---|---|
| H-1 | 0.400 |
| B-1(diameter 0.8 $\mu$m) | 0.050 |
| B-2(diameter 3.0 $\mu$m) | 0.150 |
| B-3(diameter 3.0 $\mu$m) | 0.050 |
| S-1 | 0.200 |
| Gelatin | 0.750 |
| sodium sulfodi-2-ethylhexylsuccinate | 0.006 |

In addition to the above components, to improve the storage stability, processability, resistance to pressure, antiseptic and antifungal properties, antistatic properties, and coating properties, the individual layers contained W-1 to W-4, B-4 to B-6, F-1 to F-19, lead salt, platinum salt, iridium salt, and rhodium salt.

Preparation of organic solid dispersion dye dispersion

The ExF-2 of layer 12 was dispersed by the following method.

| | |
|---|---|
| ExF-2 wet cake (comprising 17.6 mass percent water) | 2.800 kg |
| Sodium octylphenyldiethoxymethane sulfonate (31 mass percent aqueous solution) | 0.376 kg |
| F-15 (7 percent aqueous solution) | 0.011 kg |
| Water | 4.020 kg |
| Total (Adjusted to pH = 7.2 with NaOH) | 7.210 kg |

A slurry of the above-stated composition was stirred in a dissolver to obtain a crude dispersion. An agitating mill LMK4 was then used at a perimeter speed of 10 m/s, a discharge rate of 0.6 kg/min, and a 0.3 mm diameter zirconia bead fill rate of 80 percent to achieve dispersion to an absorbance ratio of 0.29, yielding a solid mictrogain dispersion. The mean grain size of the dye micrograins was 0.29 $\mu$m.

Similarly, solid dispersions of ExF-4 and ExF-7 were obtained. The mean grain size of the dye micrograins was 0.28 $\mu$m and 0.49 $\mu$m, respectively. ExF-5 was dispersed by the microprecipitation dispersion method described in Example 1 of European Patent No. 549,489A. The mean grain size was 0.06 $\mu$m.

TABLE 2

| Emulsion Name | Average iodide content (mol %) | Average equivalent spherical diameter ($\mu$m) | Aspect ratio | Average equivalent circle diameter ($\mu$m) | Grain thickness ($\mu$m) | Grain shape |
|---|---|---|---|---|---|---|
| Em-A | 4 | 0.92 | 14 | 2 | 0.14 | Tabular grain |
| Em-B | 5 | 0.8 | 12 | 1.6 | 0.13 | Tabular grain |
| Em-C | 4.7 | 0.51 | 7 | 0.85 | 0.12 | Tabular grain |
| Em-D | 3.9 | 0.37 | 2.7 | 0.4 | 0.15 | Tabular grain |
| Em-E | 5 | 0.92 | 14 | 2 | 0.14 | Tabular grain |
| Em-F | 5.5 | 0.8 | 12 | 1.6 | 0.13 | Tabular grain |
| Em-G | 4.7 | 0.51 | 7 | 0.85 | 0.12 | Tabular grain |

TABLE 2-continued

| Emulsion Name | Average iodide content (mol %) | Average equivalent spherical diameter (μm) | Aspect ratio | Average equivalent circle diameter (μm) | Grain thickness (μm) | Grain shape |
|---|---|---|---|---|---|---|
| Em-H | 3.7 | 0.49 | 3.2 | 0.58 | 0.18 | Tabular grain |
| Em-I | 2.8 | 0.29 | 1.2 | 0.27 | 0.23 | Tabular grain |
| Em-J | 5 | 0.8 | 12 | 1.6 | 0.13 | Tabular grain |
| Em-K | 3.7 | 0.47 | 3 | 0.53 | 0.18 | Tabular grain |
| Em-L | 5.5 | 1.4 | 9.8 | 2.6 | 0.27 | Tabular grain |
| Em-M | 8.8 | 0.64 | 5.2 | 0.85 | 0.16 | Tabular grain |
| Em-N | 3.7 | 0.37 | 4.6 | 0.55 | 0.12 | Tabular grain |
| Em-O | 1.8 | 0.19 | — | — | — | Cubic grain |

In Table 2, emulsions Em-A through C were obtained by adding optimal quantities of spectral sensitization pigments 1–3 and conducting optimal gold sensitization, sulfur sensitization, and selenium sensitization. Emulsion Em-J was obtained by adding optimal quantities of spectral sensitization pigments 7 and 8, and conducting optimal gold sensitization, sulfur sensitization, and selenium sensitization. Emulsion Em-L was obtained by adding optimal quantities of spectral sensitization pigments 9–11 and conducting optimal gold sensitization, sulfur sensitization, and selenium sensitization. Emulsion Em-O was obtained by adding optimal quantities of spectral sensitization pigments 10–12 and conducting optimal gold sensitization and sulfur sensitization. Emulsions Em-D, H, I, K, M, and N were obtained by adding suitable quantities of the spectral sensitization pigments listed in Table 3 and conducting optimal gold sensitization, sulfur sensitization, and selenium sensitization.

TABLE 3

| Emulsion Name | Sinsetizing Dye | Amount to be added (mol/Ag mol) |
|---|---|---|
| Em-D | Sensitizing Dye 1 | $5.44 \times 10^{-4}$ |
| | Sensitizing Dye 2 | $2.35 \times 10^{-4}$ |
| | Sensitizing Dye 3 | $7.26 \times 10^{-6}$ |
| Em-H | Sensitizing Dye 8 | $6.52 \times 10^{-4}$ |
| | Sensitizing Dye 13 | $1.35 \times 10^{-4}$ |
| | Sensitizing Dye 6 | $2.48 \times 10^{-5}$ |
| Em-I | Sensitizing Dye 8 | $6.09 \times 10^{-4}$ |
| | Sensitizing Dye 13 | $1.26 \times 10^{-4}$ |
| | Sensitizing Dye 6 | $2.32 \times 10^{-5}$ |
| Em-K | Sensitizing Dye 7 | $6.27 \times 10^{-4}$ |
| | Sensitizing Dye 8 | $2.24 \times 10^{-4}$ |
| Em-M | Sensitizing Dye 9 | $2.43 \times 10^{-4}$ |
| | Sensitizing Dye 10 | $2.43 \times 10^{-4}$ |
| | Sensitizing Dye 11 | $2.43 \times 10^{-4}$ |
| Em-N | Sensitizing Dye 9 | $3.28 \times 10^{-4}$ |
| | Sensitizing Dye 10 | $3.28 \times 10^{-4}$ |
| | Sensitizing Dye 11 | $3.28 \times 10^{-4}$ |

The sensitization pigments listed in Table 3 are given below.

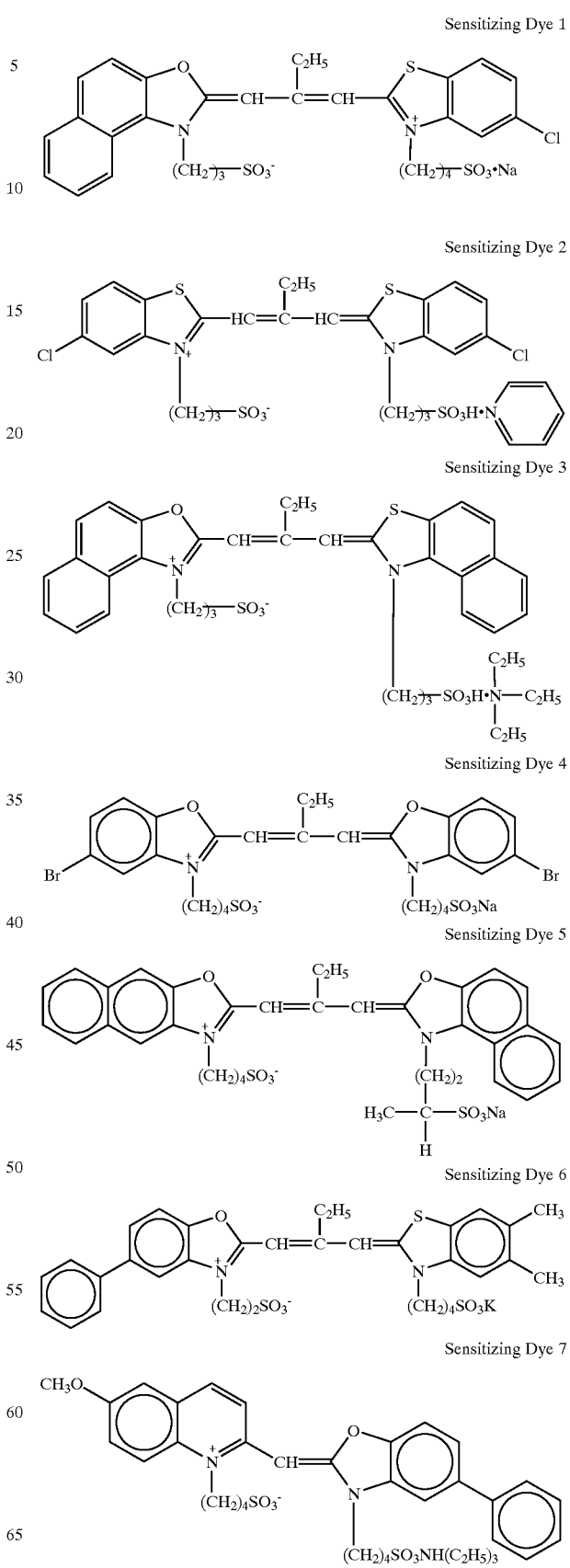

Sensitizing Dye 8

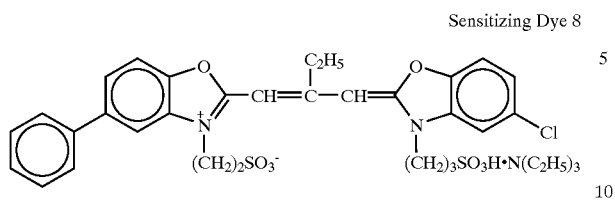

Sensitizing Dye 9

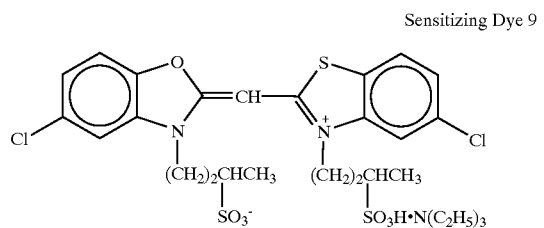

Sensitizing Dye 10

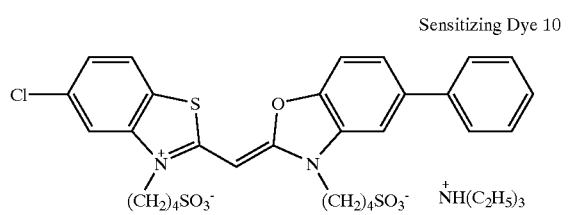

Sensitizing Dye 11

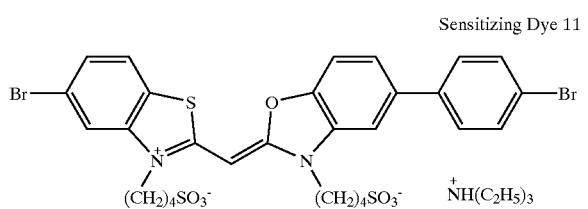

Sensitizing Dye 12

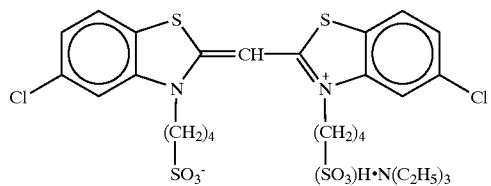

Sensitizing Dye 13

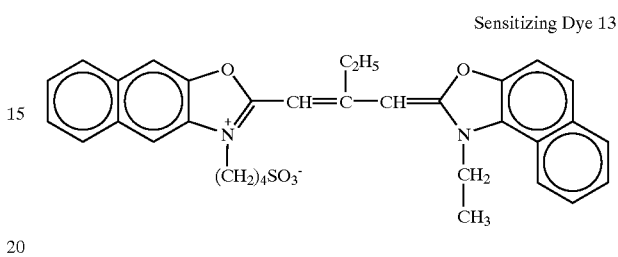

In the preparation of platelike grains, low-molecular-weight gelatin was employed according to the example described in JP-A-1-158426. Suitable quantities of Ir and Fe were incorporated into emulsions Em-A through K. Emulsions Em-L through O were reduction sensitized during grain preparation. When a high-voltage electron microscope was employed on the platelike grains, dislocation lines such as those described in JP-A-3-237450 were observed. An iodine ion-discharging agent was employed according to the example described in JP-A-6-11782 to incorporate dislocations into Emulsions Em-A through C. Silver halide grains prepared immediately prior to addition in a separate chamber having the magnetic coupling derivative stirrer described in JP-A-10-43570 were employed to incorporate dislocations in Emulsion Em-E.

The compounds employed in each layer are given below.

ExC-1

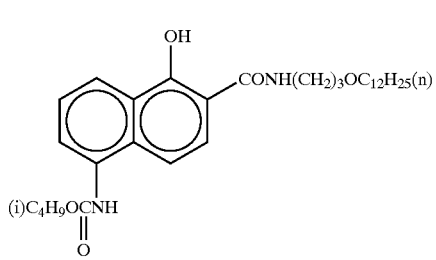

ExC-2

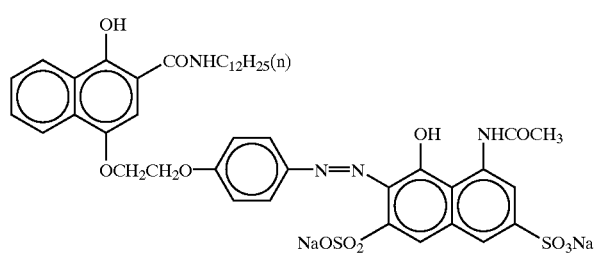

ExC-3

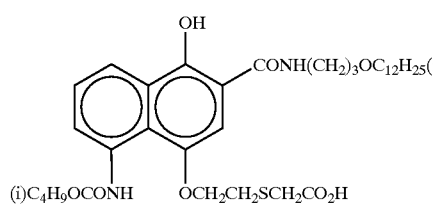

ExC-4

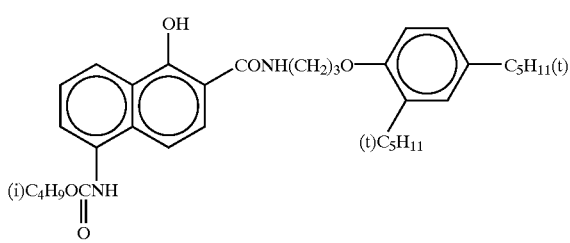

ExC-5
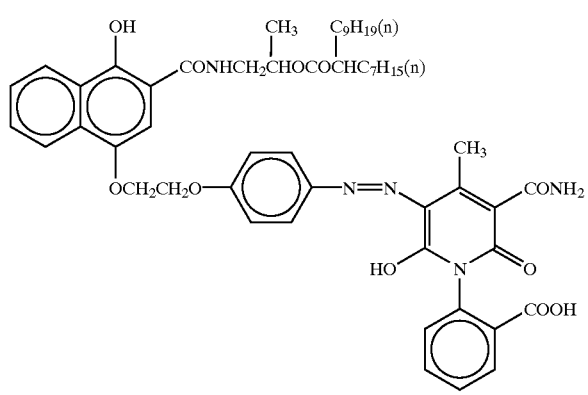
ExC-6
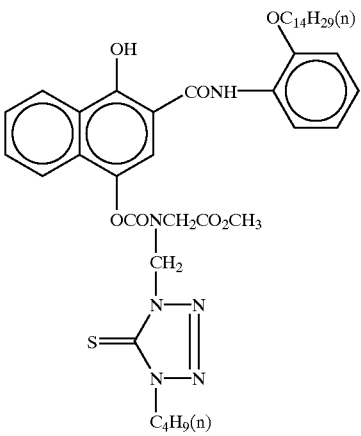
ExC-7
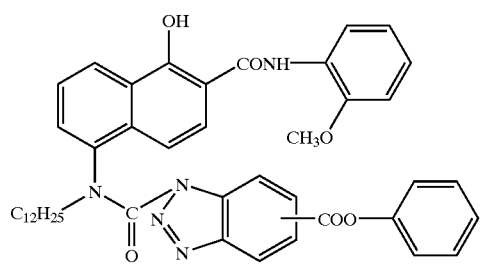
ExC-8
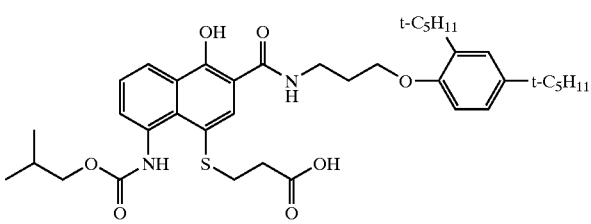
ExC-9
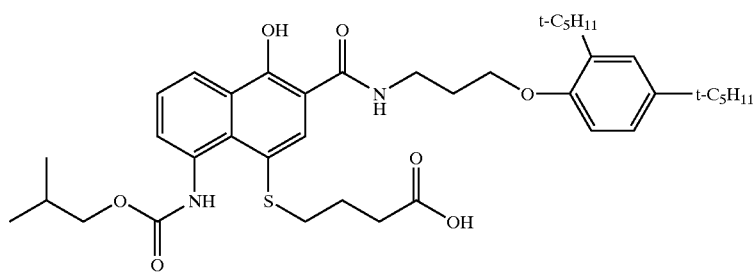
ExM-1
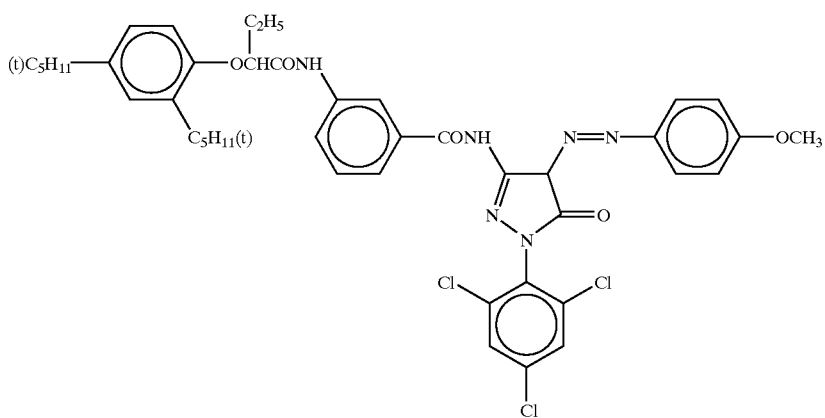

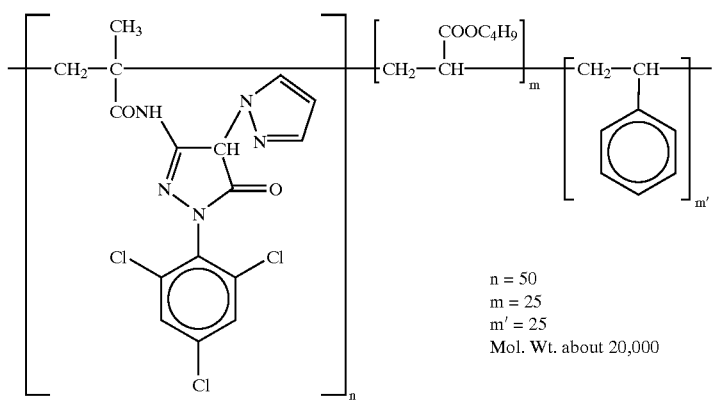
ExM-2
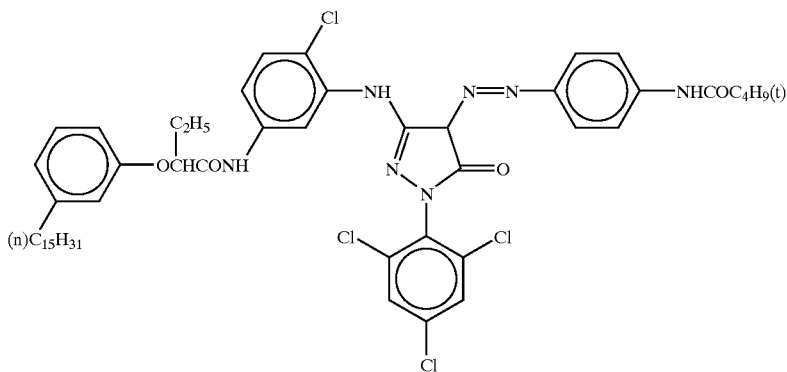
ExM-3
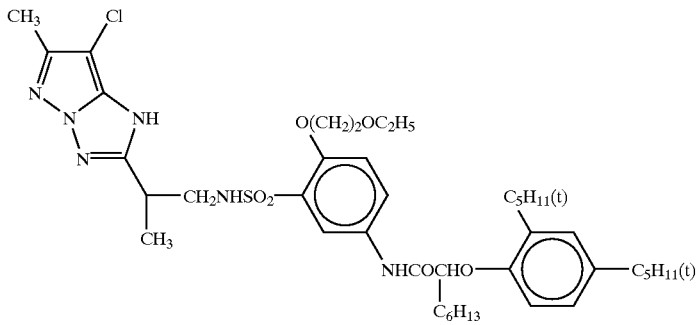
ExM-4
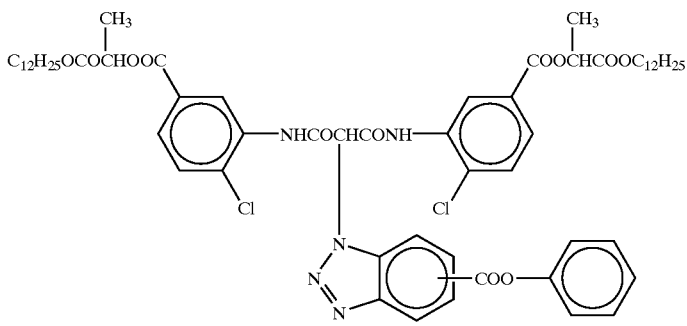
ExY-1

-continued
ExY-2
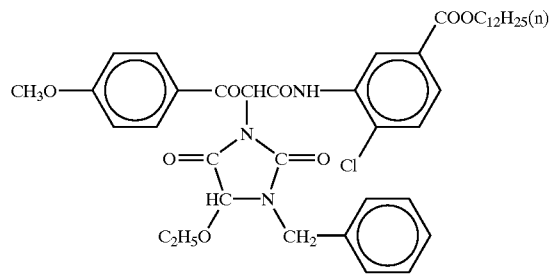
ExY-3
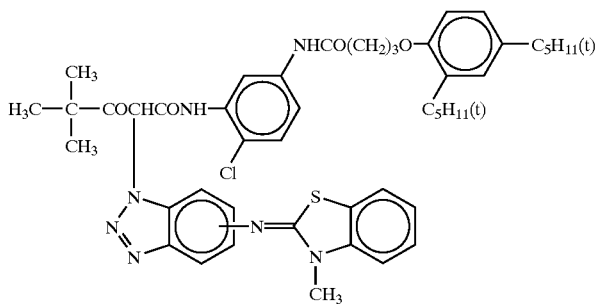
ExY-4
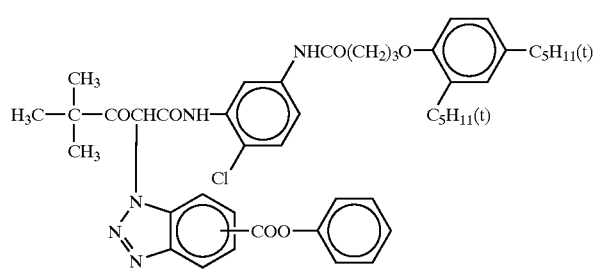
Cpd-1
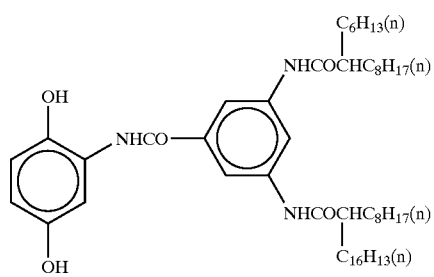
Cpd-3
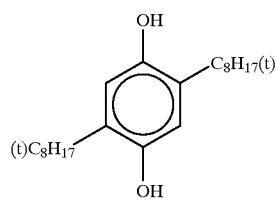
Cpd-2
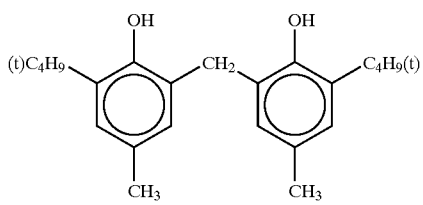
Cpd-5
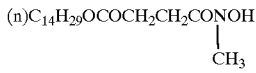
Cpd-4
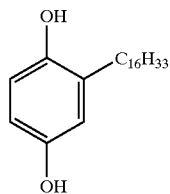
Cpd-6
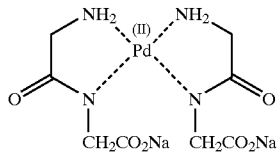
UV-1
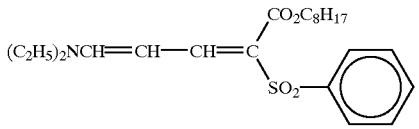
UV-2
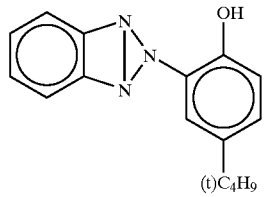
UV-3
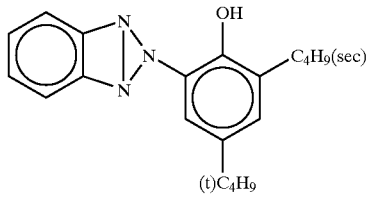

UV-4
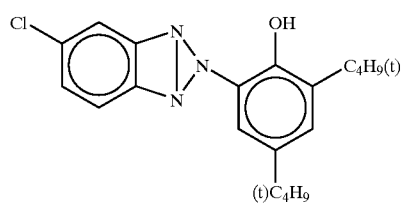
B-1
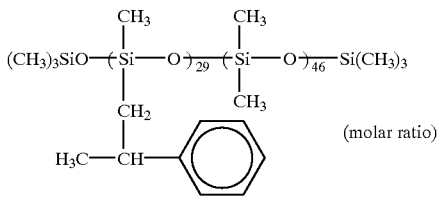
(molar ratio)
Average Molecular Weight: about 35,000
B-2
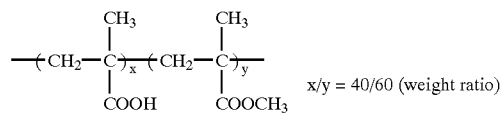 x/y = 40/60 (weight ratio)
Average Molecular Weight: about 20,000
B-3
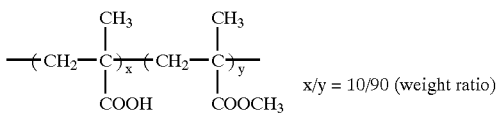 x/y = 10/90 (weight ratio)
Average Molecular Weight: about 8,000
HBS-1:
tricresyl phosphate
HBS-2:
di-n-butylphthalate
HBS-3:
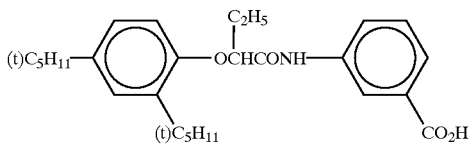
HBS-4:
tri(2-ethyl hexyl)phosphate
HBS-5
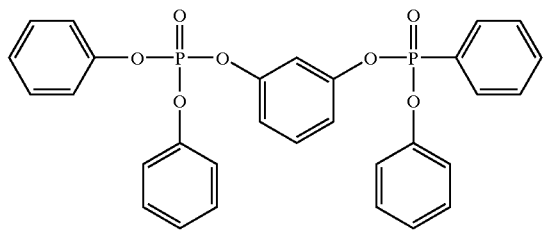
S-1
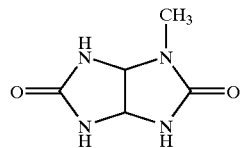
H-1
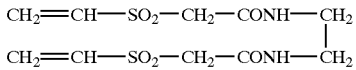
F-1
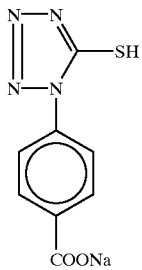
F-2
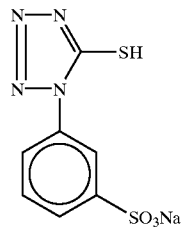
F-3
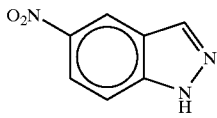
F-4

-continued
| | | | |
|---|---|---|---|
| 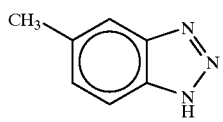 | | F-5 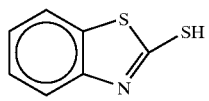 | F-6 |
| 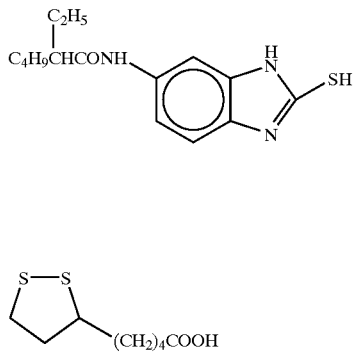 | | F-7 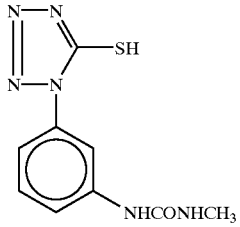 | F-8 |
| 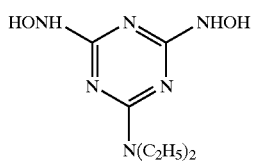 | | F-9 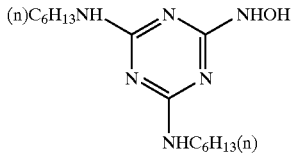 | F-10 |
|  | | F-11  | F-12 |
| 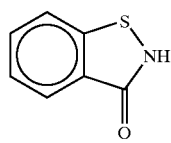 | | F-13 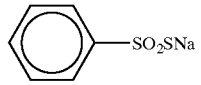 | F-14 |
| 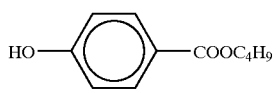 | | F-15 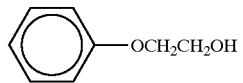 | F-16 |
| 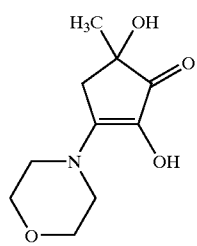 | | F-17 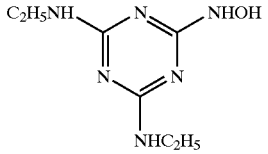 | F-18 |
| 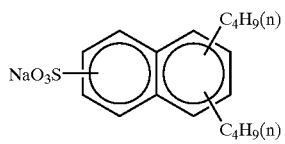 | | F-19 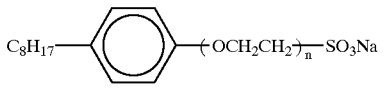  n = 2 to 4 | W-1 |
| | | W-2  | W-3 |

-continued
W-4
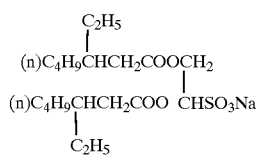
B-4
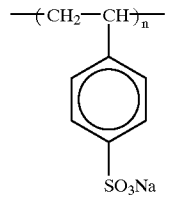
Average Molecular Weight: about 750,000
B-5
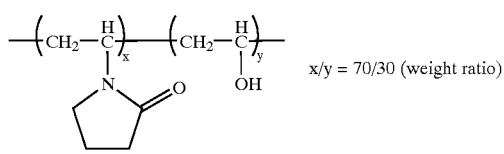
x/y = 70/30 (weight ratio)
Average Molecular Weight: about 17,000
B-6
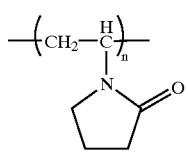
Average Molecular Weight: about 10,000
ExF-1
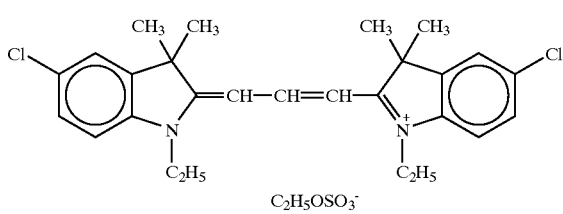
ExF-2
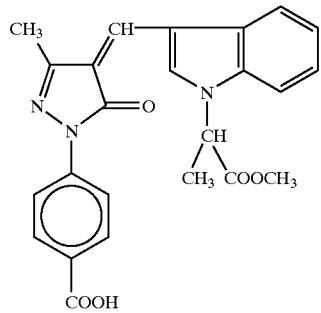
ExF-4
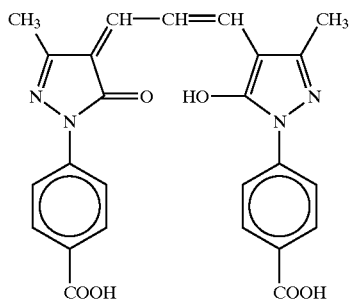
ExF-5
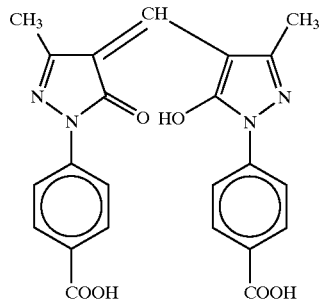
ExF-6
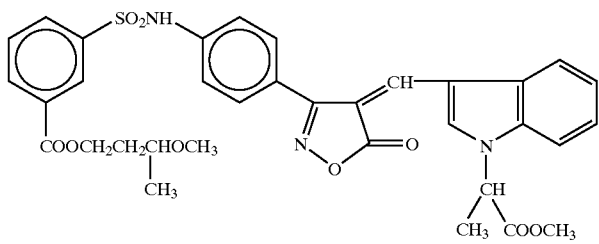
ExF-7
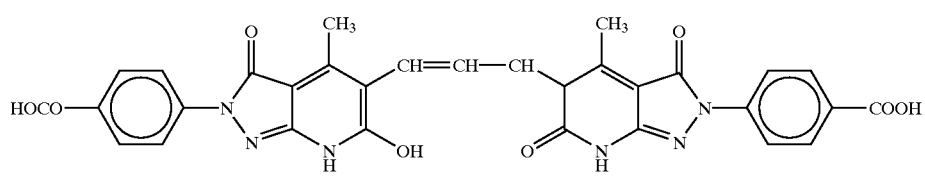

The above-described silver halide color photographic light-sensitive material was called Sample 100.

Sample 101 was prepared in the same manner as Sample 100 with the exception that 0.016 g/m² of fluorocompound FS-3 of the present invention was added as a surfactant to the 16th layer.

Samples 102–105 of the present invention and Comparative Examples 106–110 were prepared by adding the fluorocompounds and comparative example compounds shown in FIG. 4 as surfactants in place of the FS-3 in the 16th layer in homogenous amounts based on the quantity of fluorine.

<Evaluation>

(1) Electrostatic Charge Adjusting Capability Test

Electrostatic charge adjusting capability tests were conducted for prepared Samples 100–110. The level of electrostatic charge was measured in an environment of 25° C. and 10 percent relative humidity by the method of attaching with two-sided tape the surface opposite from the surface on which the emulsion was coated on samples measuring 35·120 mm, and after nipping the samples between grounded opposed rubber rollers, introducing them into a Faraday gauge. The results of measurement of the level of electrostatic charging are given as individual electrostatic charging sequence indexes. The term electrostatic charge sequence index refers to a value obtained by subtracting the level of electrostatic charging of each of Samples 101–110 from the electrostatic charge level of Sample 100 and multiplying it by $10^9$. Those samples having an electrostatic charge sequence index of less than –0.5 were determined to have adequate electrostatic charge sequence adjusting capability.

The results are given in Table 4.

TABLE 4

| Sample | Surfactant | Electrostatic Charge Sequence Index | Electrostatic Charge Adjusting Capability | Remarks |
|---|---|---|---|---|
| 101 | FS-3 | –1.5 | O | This invention |
| 102 | FS-8 | –2.3 | O | This invention |
| 103 | FS-9 | –2.1 | O | This invention |
| 104 | FS-11 | –2.8 | O | This invention |
| 105 | FS-12 | –2.7 | O | This invention |
| 106 | Comparative Compound FC-1 | –2.7 | O | Comparative Example |
| 107 | Comparative Compound FC-2 | –1.7 | O | Comparative Example |
| 108 | Comparative Compound FC-3 | –0.2 | X | Comparative Example |
| 109 | Comparative Compound FC-4 | +0.2 | X | Comparative Example |
| 110 | Comparative Compound FC-5 | –1.4 | O | Comparative Example |

From the results given in Table 4, it will be seen that in conventional fluorosurfactants, electrostatic charge adjusting capability was exhibited when the perfluoroalkyl group had a long chain. However, compounds having short-chain fluoroalkyl groups (Comparative Compound FC-3) with less than six carbon atoms and compounds having multiple short-chain fluoroalkyl groups (Comparative Compound FC-4) exhibited inadequate electrostatic charge adjusting capability. By contrast, the fluorocompounds of the present invention clearly had adequate electrostatic charge adjusting capability irrespective of whether or not the chain of the fluoroalkyl group was short.

The surface of the samples of the present invention were analyzed by X-ray photoelectron spectroscopy (XPS). Determination of the ratio of fluorine atoms/carbon atoms on the surface revealed a correlation between electrostatic charge adjustment capability and the quantity of surface fluorine. The fluorocompounds of the present invention were found to have an effective fluorine atom presence on the sample surface.

(2) Evaluation of Ability to Reduce Repelled Spots

Samples 201–210 shown in FIG. 5 were prepared employing the same structural components as before with the exceptions that the grain diameter of B-1 in the 16th layer of Samples 101–110 was made 3 μm and the quantity of fluorocompound added was made homogenous with that of Sample 101 in all samples. In the preparation of Samples 201–210, the 16th layer was formed by the slide bead application method by coating the coating solution at 1 m/sec, immediately drying it, visually counting the number of repelled spots generated on the coated film surface, and based on the value recorded, calculating the "Degree of repelled Spots". Here, the Degree of Repelled Spots is a percentage of the number of repelled spots of each sample relative to the number of repelled spots of Sample 206. The ability to reduce repelled spots was determined to be present when the number was less than 100.

The results are given in Table 5.

TABLE 5

| Sample | Surfactant | Degree of Repelled Spots | Dynamic Surface Tension (mN/s) | Remarks |
|---|---|---|---|---|
| 201 | FS-3 | 30 | 50 | This invention |
| 202 | FS-8 | 5 | 33 | This invention |
| 203 | FS-9 | 10 | 34 | This invention |
| 204 | FS-11 | 30 | 45 | This invention |
| 205 | FS-12 | 50 | 50 | This invention |
| 206 | Comparative Compound FC-1 | 100 | 54 | Comparative Example |
| 207 | Comparative Compound FC-2 | 150 | 65 | Comparative Example |
| 208 | Comparative Compound FC-3 | 20 | 58 | Comparative Example |
| 209 | Comparative Compound FC-4 | 6 | 50 | Comparative Example |
| 210 | Comparative Compound FC-5 | 120 | 60 | Comparative Example |

As can be seen from the results of Table 5, it was found that using a coating solution comprising the fluorocompound of the present invention as a surfactant reduced the number of repelled spots in all cases. That is, the fluorocompound of the present invention was found to have a good ability to reduce the occurrence of repelled spots. Furthermore, as shown in Example 1, the value of dynamic surface tension of the aqueous solution and the degree of repelled spots were found to correlate well. Combining this with the results of Table 4, the fluorocompound of the present invention clearly had both a better electrostatic charge adjusting capability and afforded better repelled spots reduction than the comparative compounds.

(3) Photographic Characteristics

Samples 101–110 were left standing for 14 hr at a temperature of 40° C. and 70 percent relative humidity, exposed for $1/100^{th}$ of a second by being passed through a continuous wedge with a color temperature of 4,800° K., and color developed as indicated below. The density of the processed samples was measured with a red filter to evaluate photographic performance. Sensitivity was evaluated as the relative value of the log of the inverse of the level of exposure displayed at the lux·second level imparting a cyan density of the fogging density plus 0.2. All of the materials had identical photographic characteristics such as sensitivity and color image density.

Developing was conducted by the following method with an Automatic Developer FP-360B made by Fuji Photographic Film Co.

However, the structure was modified so that the overflow solution from the bleach bath did not flow into the rear vat, but into the discharge tank. The steam emitting compensation means described in Public Technical Report No. 94-4992 (released by the Invention Association Corporation) was mounted on the FP-360B.

The processing steps and processing solution composition were as follows.

(Processing Steps)

| Step | Time | Temperature | Replenishment Volume | Tank Volume |
|---|---|---|---|---|
| Color development | 3 min 5 sec | 37.8° C. | 20 mL | 11.5 L |
| Bleaching | 50 sec | 38.0° C. | 5 mL | 5 L |
| Fixing (1) | 50 sec | 38.0° C. | — | 5 L |
| Fixing (2) | 50 sec | 38.0° C. | 8 mL | 5 L |
| Washing | 50 sec | 38.0° C. | 17 mL | 3 L |
| Stabilization (1) | 30 sec | 38.0° C. | — | 3 L |
| Stabilization (2) | 20 sec | 38.0° C. | 15 mL | 3 L |
| Drying | 20 sec | 60.0° C. | | |

*Replenishment level: compensation level per 1.1 m of light-sensitive material 35 mm in width (corresponding to one roll of 24 shots).

A flow from (2) to (1) was employed for the stabilizer and fixing solution. The overflow solutions during water washing were all directed into fixing bath (2). The amount of developing solution carried into the bleaching step, the amount of bleaching solution carried into the fixing step, and the amount of fixing solution carried into the water washing step were 2.5 mL, 2.0 mL, and 2.0 mL, respectively, per 1.1 m of light-sensitive material 35 mm in width. Furthermore, all the crossover times were 6 sec; this time was included in the preprocessing time.

The opening areas of the above-described processor were 100 cm² for the color developing solution, 120 cm² for the bleaching solution, and about 100 cm² for other processing solutions.

The compositions of the processing solutions are presented below.

(Color developer)

| | Tank solution (g) | Replenisher (g) |
|---|---|---|
| Diethylenetriamine | 3.0 | 3.0 |
| disodiumu catecol-3,5-disulfonate | 0.3 | 0.3 |
| Sodium sulfite | 3.9 | 5.3 |
| Potassium carbonate | 39.0 | 39.0 |
| Disodium-N,N-bis(2-sulfonateethyl)hydroxylamine | 1.5 | 2.0 |
| Potassium bromide | 1.3 | 0.3 |
| Potassium iodide | 1.3 mg | — |
| 4-hydroxy-6-methyl-1,3,3a,7-tetrazaindene | 0.05 | — |
| hydroxylamine sulfonic acid | 2.4 | 3.3 |
| 2-methyl-4-[N-ethyl-N-(β-hydroxyethyl)amino]aniline sulfate | 4.5 | 6.5 |
| Water to make | 1.0 L | 1.0 L |
| pH (controlled by potassium hydroxide and sulfuric acid) | 10.05 | 10.18 |

(Bleaching solution)

| | Tank solution (g) | Replenisher (g) |
|---|---|---|
| Ferric ammonium 1,3-diaminopropanetetra acetate monohydrate | 113 | 170 |
| Ammonium bromide | 70 | 105 |
| Ammonium nitrate | 14 | 21 |
| Succinic acid | 34.0 | 51.0 |
| Maleic acid | 28 | 42 |
| Water to make | 1.0 L | 1.0 L |
| pH (controlled by ammonia water and nitric acid) | 4.6 | 4.0 |

(Fixing (1) Tank Solution)

A 5:95 (volume ratio) mixture of the above bleaching tank solution and the following fixing tank solution (pH 6.8).

(Fixer(2))

| | Tank solution (g) | Replenisher (g) |
|---|---|---|
| Aqueous ammonium thiosulfate solution (750 g/L) | 240 mL | 720 mL |
| Imidazole | 7 | 21 |
| Ammonium methane thiosulfonate | 5 | 15 |
| Ammonium methane sulfinate | 10 | 30 |
| Ethylenediamine tetraacetic acid | 13 | 39 |
| Water to make | 1.0 L | 1.0 L |
| pH (controlled by ammonia water and acetic acid) | 74 | 745 |

(Washing water) Common to Tank Solution and Replenisher

Tap water was supplied to a mixed-bed column filled with an H type strongly acidic cation exchange resin (Amberlite IR-120B: available from Rohm & Haas Co.) and an OH type strongly basic anion exchange resin (Amberlite IR-400) to set the concentrations of calcium and magnesium to be 3 mg/L, or less. Subsequently, 20 mg/L of sodium isocyanuric acid dichloride and 150 mg/L of sodium sulfate were added. The pH of the solution ranged from 6.5 to 7.5.

| (Stabilizer) Common to Tank Solution and Replenisher | |
|---|---|
| | unit (g) |
| Sodium p-toluenesulfate | 0.03 |
| Polyoxyethylene-p-monononylphenylether (average polymerization degree 10) | 0.2 |
| 1,2-benzoisothiazoline-3-one.sodium | 0.10 |
| Disodium ethylenediaminetetraacetate | 0.05 |
| 1,2,4-triazole | 1.3 |
| 1,4-bis(1,2,4-triazole-1-isomethyl)piperazine | 0.75 |
| Water to make | 1 L |
| PH | 8.5 |

The present invention as described above provides a new fluorocompound and surfactant with good surface orientation characteristics and permitting uniform film formation when employed to form films while having a short perfluoroalkyl group. Furthermore, the present invention provides a coating composition permitting the formation of uniform films having antistatic properties. Still further, the present invention provides a silver halide photographic light-sensitive material affording antistatic properties while permitting stable manufacturing.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A silver halide photographic light-sensitive material having at least one layer comprising a light-sensitive silver halide emulsion layer on a support and comprising a compound denoted by general formula (1) below in at least one layer thereof

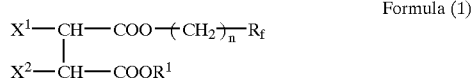

Formula (1)

(wherein $R^1$ denotes a substituted or unsubstituted alkyl group having a total of at least six carbon atoms, with $R^1$ not being an alkyl group substituted with a fluorine atom; $R_f$ denotes a perfluoroalkyl group having not more than six carbon atoms; either $X^1$ or $X^2$ denotes a hydrogen atom and the other denotes $SO_3M$; M denotes a cation; and n denotes an integer of not less than 1).

2. The silver halide photographic light-sensitive material of claim 1 wherein there is a light-insensitive hydrophilic colloidal layer in the outermost layer and said outermost layer comprises the compound denoted by said general formula (1).

3. The silver halide photographic light-sensitive material of claim 1 wherein at least one of the silver halide emulsions comprised in said silver halide emulsion layers is an emulsion in which not less than 50 percent of the total projection area of the silver halide grains is made up of grains with an aspect ratio of not less than 3.

4. The silver halide photographic light-sensitive material of claim 1 wherein at least one of the silver halide comprised in said silver halide emulsion layers is iodobromide, iodochloride, bromochloride or iodochlorobromide.

5. The silver halide photographic light-sensitive material of claim 1 wherein at least one of the silver halide emulsions comprised in said silver halide emulsion layers is subjected to at least one from among sulfur sensitization, selenium sensitization, gold sensitization, palladium sensitization, or noble metal sensitization.

6. The silver halide photographic light-sensitive material of claim 1 wherein in said general formula (1), $R^1$ denotes a substituted or unsubstituted alkyl group with a total of 6–24 carbon atoms.

7. The silver halide photographic light-sensitive material of claim 1 wherein in said general formula (1), n denotes an integer of 1–4.

8. The silver halide photographic light-sensitive material of claim 1 wherein in said general formula (1), M denotes an alkali metal ion, alkali earth metal ion or ammonium ion.

9. The silver halide photographic light-sensitive material of claim 1, wherein in said general formula (1), $R^1$ denotes a substituted or unsubstituted alkyl group with a total of 6–18 carbon atoms.

10. The silver halide photographic light-sensitive material of claim 1, wherein in said general formula (1), $R^1$ denotes an unsubstituted alkyl group with a total of 8–10 carbon atoms.

11. The silver halide photographic light-sensitive material of claim 1, wherein in said general formula (1), n denotes 1 or 2.

12. The silver halide photographic light-sensitive material of claim 1, wherein in said general formula (1), when n=1, $R_f$ denotes a heptafluoro-n-propyl group or nonafluoro-n-butyl group, and when n=2, $R_f$ denotes a nonafluoro-n-butyl group.

13. The silver halide photographic light-sensitive material of claim 6, wherein unsubstituted alkyl groups having 6–24 carbon atoms are selected from the group consisting of n-hexyl groups, n-heptyl groups, n-octyl groups, tert-octyl groups, 2-ethylhexyl groups, n-nonyl groups, 1,1,3-trimethylhexyl groups, n-decyl groups, n-dodecyl groups, cetyl groups, hexadecyl groups, 2-hexyldecyl groups, octadecyl groups, eicosyl groups, 2-octyldodecyl groups, docosyl groups, tetracosyl groups, 2-decyltetradecyl groups, tricosyl groups, cyclohexyl groups, and cycloheptyl groups.

14. The silver halide photographic light-sensitive material of claim 6, wherein substituted alkyl groups having 6–24 carbon atoms are selected from the group consisting of 2-hexenyl groups, oleyl groups, linoleyl groups, linolenyl groups, benzyl groups, β-phenethyl groups, 4-phenylbutyl groups, 6-phenoxyhexyl groups, 12-phenyldodecyl groups, 18-phenyloctadecyl groups, 12-(p-chlorophenyl)dodecyl groups, and 2-(phosphoric diphenyl)ethyl groups.

15. The silver halide photographic light-sensitive material of claim 1, wherein $R_f$ is a perfluoroalkyl group which is selected from the group consisting of trifluoromethyl groups, pentafluoroethyl groups, heptafluoro-n-propyl groups, heptafluoroisopropyl groups, nonafluoro-n-butyl groups, undecafluoro-n-pentyl groups, tridecafluoro-n-hexyl groups, and undecafluorocyclohexyl groups.

16. The silver halide photographic light-sensitive material of claim 1, wherein $R_f$ is a perfluoroalkyl group having 2–4 carbon atoms.

17. The silver halide photographic light-sensitive material of claim 1, wherein $R_f$ is a perfluoroalkyl group which is selected from the group consisting of pentafluoroethyl groups, heptafluoro-n-propyl groups, heptafluoroisopropyl groups, and nonafluoro-n-butyl groups.

* * * * *